United States Patent
Lu et al.

(10) Patent No.: US 11,053,237 B2
(45) Date of Patent: Jul. 6, 2021

(54) PROCESS FOR THE MANUFACTURE OF 6-ALKYNYL-PYRIDINE DERIVATIVES

(71) Applicant: BOEHRINGER INGELHEIM INTERNATIONAL GMBH, Ingelheim am Rhein (DE)

(72) Inventors: Guanghua Lu, Ingelheim am Rhein (DE); Guenther Huchler, Hochdorf (DE); Thomas Krueger, Kisslegg (DE); Michael Pangerl, Ingelheim am Rhein (DE); Marco Santagostino, Mittelbiberach (DE); Jean-Nicolas Desrosiers, Southbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/301,213

(22) PCT Filed: May 17, 2017

(86) PCT No.: PCT/EP2017/061885
§ 371 (c)(1),
(2) Date: Nov. 13, 2018

(87) PCT Pub. No.: WO2017/198794
PCT Pub. Date: Nov. 23, 2017

(65) Prior Publication Data
US 2019/0308967 A1    Oct. 10, 2019

(30) Foreign Application Priority Data
May 19, 2016  (EP) .................................. 16170489

(51) Int. Cl.
*C07D 471/04* (2006.01)
*C07D 213/73* (2006.01)
*C07D 215/06* (2006.01)
*C07D 217/04* (2006.01)
*C07D 401/10* (2006.01)
*C07D 217/24* (2006.01)
*C07D 213/74* (2006.01)
*C07D 401/06* (2006.01)

(52) U.S. Cl.
CPC ......... *C07D 471/04* (2013.01); *C07D 213/73* (2013.01); *C07D 213/74* (2013.01); *C07D 215/06* (2013.01); *C07D 217/04* (2013.01); *C07D 217/24* (2013.01); *C07D 401/06* (2013.01); *C07D 401/10* (2013.01)

(58) Field of Classification Search
CPC .................................................... C07D 471/04
USPC .......................................................... 546/121
See application file for complete search history.

(56) References Cited

U.S. PATENT DOCUMENTS

| | | |
|---|---|---|
| 8,859,541 B2 | 10/2014 | Reiser et al. |
| 9,249,151 B2 | 2/2016 | Reiser et al. |
| 9,278,978 B2 | 3/2016 | Reiser et al. |
| 9,481,673 B2 | 11/2016 | Reiser |
| 9,801,871 B2 | 10/2017 | Reiser |
| 2013/0225567 A1 | 8/2013 | Reiser et al. |
| 2015/0057286 A1 | 2/2015 | Reiser et al. |
| 2015/0057295 A1 | 2/2015 | Reiser et al. |

FOREIGN PATENT DOCUMENTS

| | | |
|---|---|---|
| WO | 2006113147 A2 | 10/2006 |
| WO | 2006133147 A2 | 12/2006 |
| WO | 2007101347 A1 | 9/2007 |
| WO | 2008073306 A1 | 6/2008 |
| WO | 2013127729 A1 | 9/2013 |
| WO | 2016023858 A1 | 2/2016 |

OTHER PUBLICATIONS

Bruno et al., "Targeting cytochrome P450 enzymes: A new approach in anti-cancer drug development", Science Direct, vol. 15, 2007, pp. 5047-5060.
Choy, Pui Ying et al. "Palladium-Catalyzed Sonogashira Coupling of Aryl Mesylates and Tosylates" (2010) Chemistry A European Journal, vol. 16, 9982-9985.
Hansen, Marvin M. et al. "Boronic Acids and Derivatives—Probing the Structure—Activity Relationships for Mutagenicity" (2015) Org. Process Res. Dev., vol. 19, 1507-1516.
International Search Report PCT/EP2017/061885 dated Jul. 17, 2017.
Jordan et al., Binding of Carboxylic Acids by Fluorescent Pyridyl Ureas, J. Org Chem, 2010, 75, pp. 8450-8456.
Zhichkin, Paul E. et al. "The Use of Formamidine Protection for the Derivatization of Amiobenzoic Acids" (2008) Journal of Organic Chemistry, vol. 73, 8954-8959.

*Primary Examiner* — Patricia L Morris
(74) *Attorney, Agent, or Firm* — Philip I. Datlow

(57) ABSTRACT

The application includes a description of novel intermediates, of new manufacturing steps resulting in a novel and improved process for producing the intermediates and the final compounds, i.e., 6-alkynyl-pyridine derivatives. The intermediates of the invention are useful to produce 6-alkynyl-pyridine derivatives, which compounds are useful for the treatment of cancer.

6 Claims, No Drawings

PROCESS FOR THE MANUFACTURE OF 6-ALKYNYL-PYRIDINE DERIVATIVES

The present invention relates to a process for the manufacture of 6-alkynyl-pyridine imidazopyridine derivatives and a pharmaceutically acceptable salt thereof. More specifically, the process of the invention relates to a process for the synthesis of compounds of Formula I, II or III,

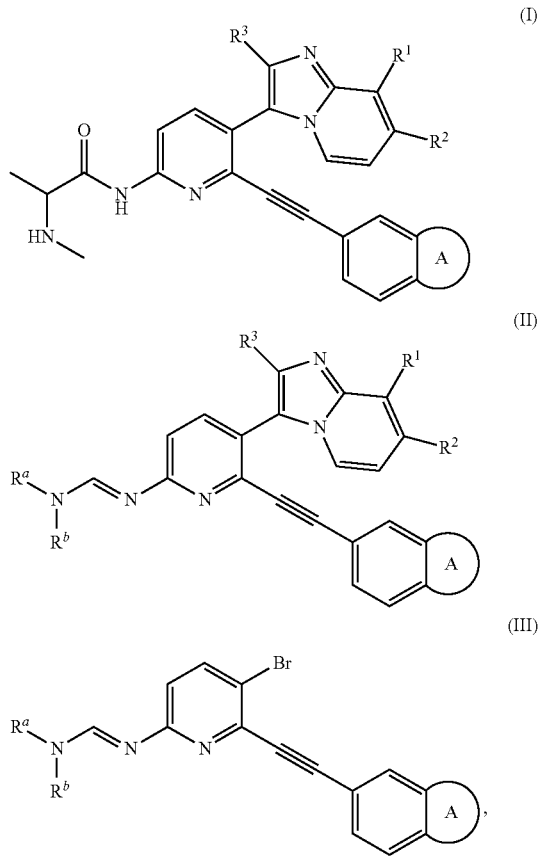

wherein the groups $R^1$ to $R^3$, $R^a$ and $R^b$ are defined herein below, and to new intermediates of this process.

The application includes a description of novel intermediates, of new manufacturing steps resulting in a novel and improved process for producing the intermediates and the final compounds, i.e., 6-alkynyl-pyridine derivatives. The intermediates of the invention are useful to produce 6-alkynyl-pyridine derivatives, which compounds are useful for the treatment of cancer. In more details, the process of the invention relates to the synthesis of the compounds of formula

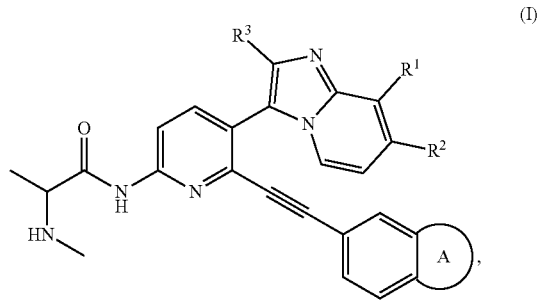

wherein
A is absent or is a 6-membered nitrogen containing heteroaryl optionally substituted with a —$C_{1-3}$alkyl group;
$R^1$ is selected from hydrogen, —$C_{1-3}$alkyl and halogen;
$R^2$ is selected from hydrogen, —$C_{1-3}$alkyl and halogen;
$R^3$ is selected from —$C_{1-3}$alkyl and 5- or 6-membered heteroaryl optionally substituted with —$C_{1-3}$alkyl or —O—$C_{1-3}$alkyl.

In another embodiment, the process of the invention relates to the synthesis of compounds of formula

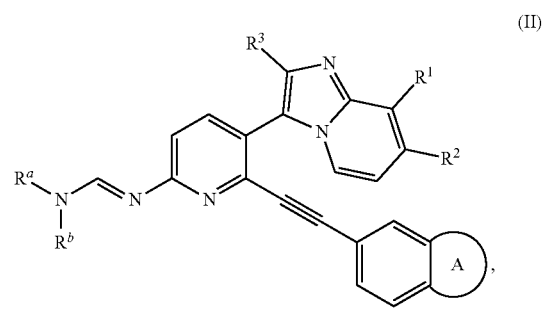

wherein
A is absent or is a 6-membered nitrogen containing heteroaryl optionally substituted with a —$C_{1-3}$alkyl group;
$R^1$ is selected from hydrogen, —$C_{1-3}$alkyl and halogen;
$R^2$ is selected from hydrogen, —$C_{1-3}$alkyl and halogen;
$R^3$ is selected from —$C_{1-3}$alkyl and 5- or 6-membered heteroaryl optionally substituted with —$C_{1-3}$alkyl or —O—$C_{1-3}$alkyl;
$R^a$ and $R^b$ are the same or different selected from —$C_{1-4}$alkyl and —$CH_2$-phenyl; or $R^a$ and $R^b$ together form a 5- to 7-membered saturated heterocyclyl attached via the nitrogen atom.

In another embodiment, the process of the invention relates to the synthesis of compounds of formula

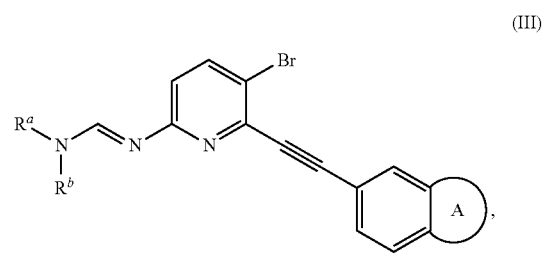

wherein
A is absent or is a 6-membered nitrogen containing heteroaryl optionally substituted with a —$C_{1-3}$alkyl group;
$R^a$ and $R^b$ are the same or different selected from —$C_{1-4}$alkyl and —$CH_2$-phenyl; or $R^a$ and $R^b$ together form a 5- to 7-membered saturated heterocyclyl attached via the nitrogen atom.

BACKGROUND TO THE INVENTION

6-Alkynyl-pyridine derivatives and their salts are known from the following patent and patent applications: U.S. Pat. No. 8,859,541, WO 2013/127729, WO 2016/023858. These patent applications disclose the compounds, a process for their manufacture and the use of the compounds or their salts in a pharmaceutical composition to treat oncological or non-oncological diseases via inhibition of the proliferation of target cells, alone or in combination with further therapeutic agents. The mechanism of action by which the proliferation of the target cells occurs is essentially a protein-protein interaction, and especially a IAP-SMAC inhibition.
U.S. Pat. No. 8,859,541, WO 2013/127729 and WO 2016/023858 describe a process for the synthesis of 6-alkynyl-pyridine derivatives, which is summarized in Scheme I below.
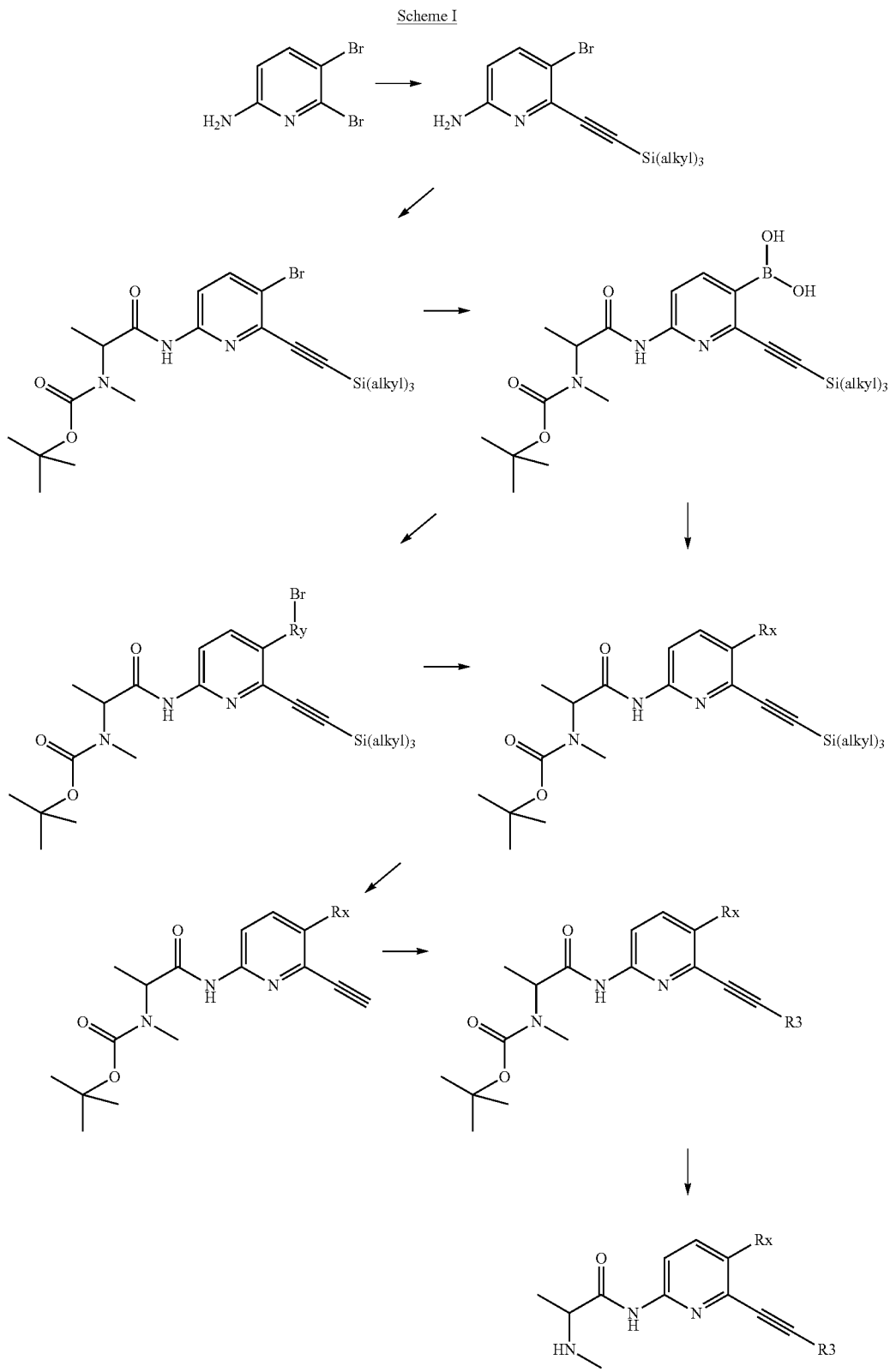
Scheme I Specifically, the method of the prior art comprises a Sonogashira cross coupling reaction at the C-6 position of a pyridine ring between 5,6-dibromo-pyridin-2-yl-amine and a trialkylsilyl acetylene to give a Si(alkyl)$_3$ protected 6-alkynyl-pyridine. This is in turn acylated at the NH$_2$ moiety on C-2 using a 2-[methyl-[(2-methylpropan-2-yl)oxycarbonyl] amino]propanoic acid. Thereafter, an imidazo[1,2-a]pyridine substituent (R$_x$ or R$_y$Br) is installed at the C-5 position of the pyridine ring by a two-step sequence comprising a Miyaura borylation followed by a Suzuki cross coupling. After appropriate functionalization of the imidazo[1,2-a] pyridine moiety (R$_y$Br to R$_x$), the synthetic route continues by removing the silicon protecting group on the alkyne moiety, which eventually allows to implement a second Sonogashira cross coupling to install the R$^3$ group before removing the N-Boc protecting group in order to complete the synthesis.

The process described in the prior art has the following disadvantages: First of all, boronic acid derivatives are used. Furthermore, five of the intermediates bear the expensive trialkylsilyl group, and these intermediates can be purified only via chromatography.

Accordingly, the process described in the prior art is not well suited to technical use on an industrial scale because of the laborious purification step and the boronic acid derivatives as well as the trialkylsilyl group, which are difficult to handle.

As it will be clear below, the process of the invention does not only overcome the above mentioned disadvantages but it also shows improvements to the process described in the prior art. Hence, the process in accordance with the present invention presents amongst others the following remarkable advantages when compared to the processes already described in the prior art:

A first advantage of the process of the invention is that it is more convergent. In fact, the process of the prior art is based on a (seven) eight-step linear synthesis whereas the new synthesis is more convergent resulting in only six linear steps, thus improving the overall synthetic efficiency and throughput.

A second advantage is that the improved process avoids the use of boronic acids intermediates (or their esters) and of the diboron compounds used for their preparation via Miyaura borylation. As also stated above, this class of compounds is known to pose a health risk associated with their handling. (*Org. Process Res. Dev.* 2015, 19, 1507-1516). This can be avoided using the process of the invention.

A third advantage is that the improved process makes use of a N,N-dimethylformamidine protecting group (*J. Org. Chem.*, 2008, 73 (22), 8954-8959) to mask the —NH$_2$ functionality on the pyridine core. This protecting group is very easy to install, surprisingly stable under the used reaction conditions and is easy to remove under a variety of conditions compatible with the presence of an alkyne moiety. In addition the N,N-dimethylformamidine protecting group allows cross coupling reactions using basic organometallic reagents, such as organozinc compounds and proved to be essential for direct arylation procedure using imidazo[1,2-a]pyridines as nucleophiles.

A fourth advantage is that in the process of the invention the polyaromatic core is prepared upstream in the synthetic sequence using conditions which are amenable for the large scale production and are more friendly towards the environment than the processes already known from the prior art. Thus, the steps leading to pivotal intermediates III (see Scheme II) are conducted at high concentrations. This implies a reduction of volume-time output (VTO) which correlates inversely with the cost of plant occupancy and reduced solvent and waste costs. Also, (poly)aromatic intermediates lacking the 2-[methyl-[(2-methylpropan-2-yl)oxycarbonyl]amino]propanoyl and the lipophilic tri(propan-2-yl)silyl moieties like the intermediates A-M exemplified in the improved process are in general highly crystalline compounds and their purification can be mainly conducted via crystallization with obvious benefits over the column chromatography purification method which is necessary according to above-mentioned patent applications.

A fifth advantage of the improved process is an extremely limited use of the labile trialkylsilyl protecting groups. Thus, a trimethylsilyl group is used as temporary protecting group only for the preparation of the intermediate E1. In the original process the trialkylsilyl protecting group is introduced at the very beginning and is maintained for most of the synthetic sequence. Thus, the use of expensive ethynyltri(propan-2-yl)silane is necessary to avoid undesired deprotection along the synthetic sequence.

A sixth advantage is that while in the above-mentioned patent applications the expensive and sensitive 2-[methyl-[(2-methylpropan-2-yl)oxycarbonyl]amino]propanoyl moiety is introduced at the very beginning of the synthetic sequence, in the improved process this is installed at the very end of the synthesis. This implies an economic advantage, an increased robustness of the preparations with a much reduced risk of racemization in case an enatiopure 2-[methyl-[(2-methylpropan-2-yl)-oxycarbonyl]amino]propanoic is used and reduced formation of side products under the used experimental conditions.

DETAILED DESCRIPTION OF THE INVENTION

Thus, the present inventors have accomplished the present invention by developing a novel method for the large scale preparation in high yield of 6-alkynyl-pyridine compounds and intermediates en route to their synthesis.

The process in accordance with the present invention is a convergent process and presents several alternatives, as shown in the following Scheme II and using the following nomenclature.

General Description of the Process of the Invention

In a first embodiment, the invention relates to a process for the synthesis of compounds of formula

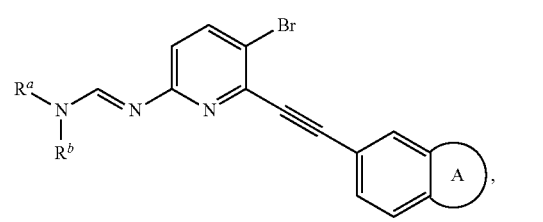

(III)

wherein

A is absent or is a 6-membered nitrogen containing heteroaryl optionally substituted with a —C$_{1-3}$alkyl group;

R$^a$ and R$^b$ are the same or different selected from —C$_{1-4}$ alkyl and —CH$_2$-phenyl; or R$^a$ and R$^b$ together form a 5- to 7-membered saturated heterocyclyl attached via the nitrogen atom;

the process comprising the steps of:
obtaining the compound of formula

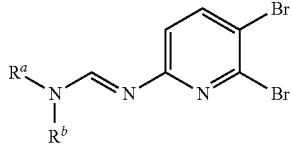
(B)

by reacting 5,6-dibromo-pyridin-2-yl-amine with a 1,1-dialkoxy-N,N-dialkylmethyl-amine of the formula $(R^zO)_2$—$CHN(R^a,R^b)$, wherein $R^z$ is a —$C_{1-3}$alkyl group;

reacting the compound of formula

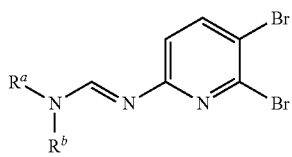
(B)

with a compound of formula

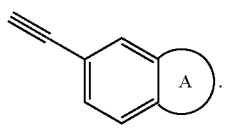
(E)

In a second embodiment the invention relates to a process for the synthesis of a compound of formula

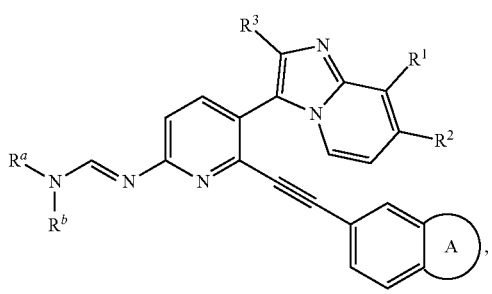
(II)

comprising the steps of
preparing the compound of formula

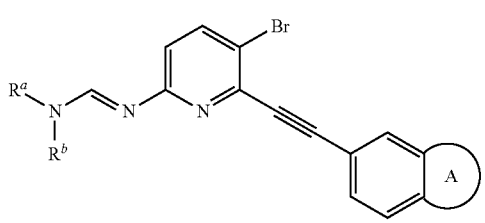
(III)

according to the process of the first embodiment;

reacting the compound of formula

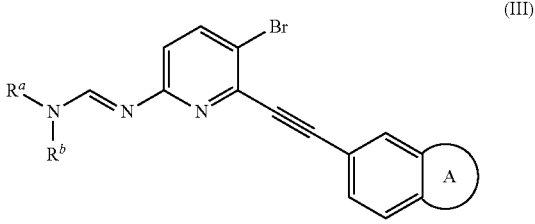
(III)

with a compound of formula

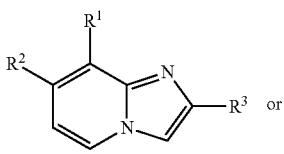
(J)

or

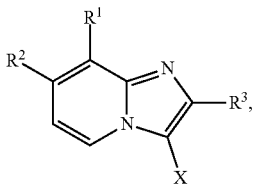
(K)

wherein
A is absent or is a 6-membered nitrogen containing heteroaryl optionally substituted with a —$C_{1-3}$alkyl group;
$R^1$ is selected from hydrogen, —$C_{1-3}$alkyl and halogen;
$R^2$ is selected from hydrogen, —$C_{1-3}$alkyl and halogen;
$R^3$ is selected from —$C_{1-3}$alkyl and 5- or 6-membered heteroaryl optionally substituted with —$C_{1-3}$alkyl or —O—$C_{1-3}$alkyl;
X is halogen;
$R^a$ and $R^b$ are the same or different selected from —$C_{1-4}$ alkyl and —$CH_2$-phenyl; or $R^a$ and $R^b$ together form a 5- to 7-membered saturated heterocyclyl attached via the nitrogen atom.

In a third embodiment the invention relates to a process for the synthesis of a compound of formula

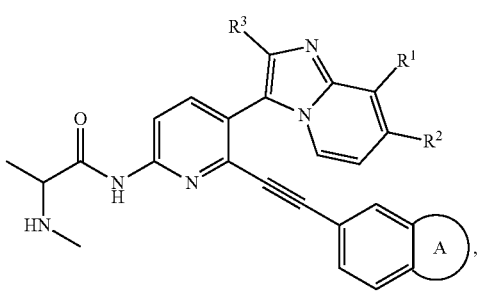
(I)

wherein
A is absent or is a 6-membered nitrogen containing heteroaryl optionally substituted with a —$C_{1-3}$alkyl group;
$R^1$ is selected from hydrogen, —$C_{1-3}$alkyl and halogen;
$R^2$ is selected from hydrogen, —$C_{1-3}$alkyl and halogen;

R³ is selected from —C₁₋₃alkyl and 5- or 6-membered heteroaryl optionally substituted with —C₁₋₃alkyl or —O—C₁₋₃alkyl;
comprising the steps of
preparing the compound of formula (II)

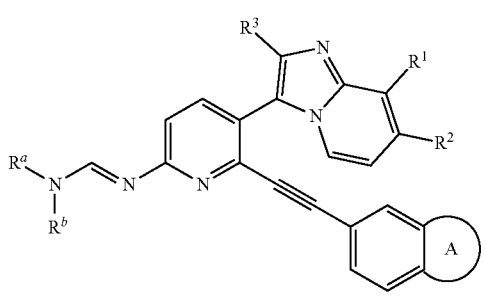

according to the process of the second embodiment, wherein
R^a and R^b are the same or different selected from —C₁₋₄ alkyl and —CH₂-phenyl; or R^a and R^b together form a 5- to 7-membered heterocycloalkyl attached via the nitrogen atom,
deprotecting the compound of formula II to form a compound of formula (M)

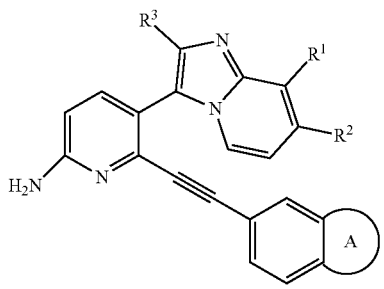

forming a compound of formula (N)

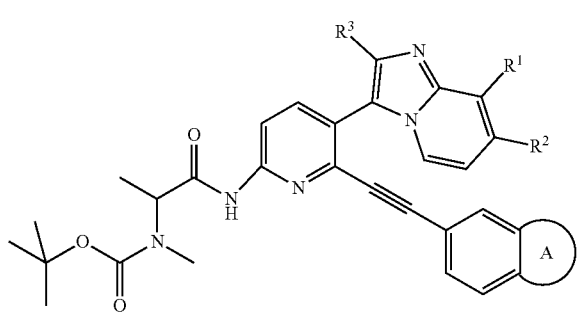

by coupling a compound of formula M with 2-[methyl-[(2-methylpropan-2-yl)oxycarbonyl]amino]propanoic acid, wherein the 2-[methyl-[(2-methylpropan-2-yl) oxycarbonyl]amino]propanoic acid is racemic, (S)-2-[methyl-[(2-methylpropan-2-yl)oxycarbonyl]amino] propanoic acid or (R)-2-[methyl-[(2-methylpropan-2-yl)oxycarbonyl]amino]propanoic acid;

deprotecting the compound of formula (N)

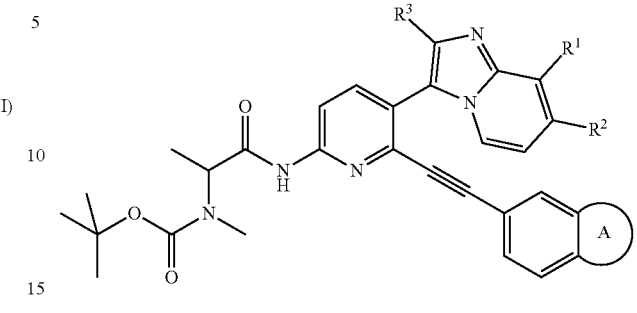

to obtain the compound of formula (I)

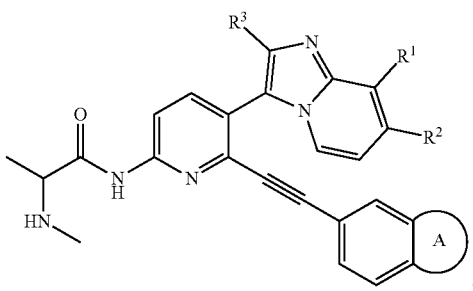

In a preferred embodiment of the invention, a compound of formula (E)

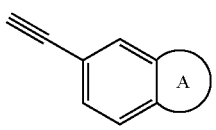

is obtained by deprotection of a compound of formula (H)

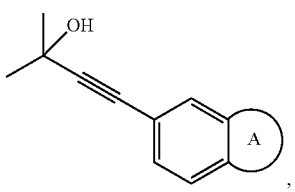

wherein
A is absent or is a 6-membered nitrogen containing heteroaryl optionally substituted with a —C₁₋₃alkyl group.
In another preferred embodiment of the invention, an intermediate of formula (H)

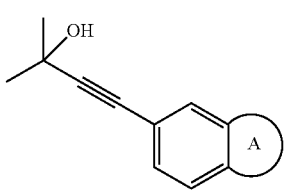

is obtained by reacting

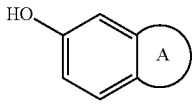
(F)

with toluenesulfonic acid chloride or benzensulfonic acid chloride to obtain

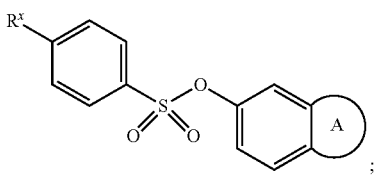
(G)

further reacting G with 2-methyl-3-butyn-2-ol to obtain a compound of formula

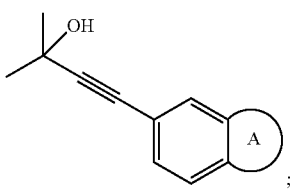
(H)

wherein
$R^x$ denotes H or —$C_{1-3}$alkyl;

A is absent or is a 6-membered nitrogen containing heteroaryl optionally substituted with a —$C_{1-3}$alkyl group, preferably —$CH_3$.

In a further preferred embodiment of the invention, $R^x$ denotes H or —$CH_3$.

In another preferred embodiment of the invention, the intermediate

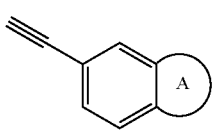
(E)

is obtained
by reacting a compound of formula

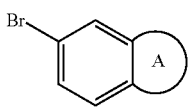
(D)

with —$C_{1-3}$ trialkylsilylacetylene, preferably trimethylsilylacetylene, to obtain, after deprotection of the resulting intermediate, a compound of formula E; or by reacting a compound of formula

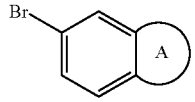
(D)

with 2-methyl-3-butyn-2-ol to obtain a compound of formula

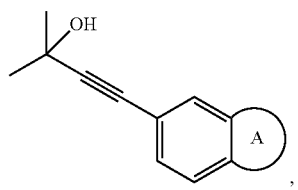
(H)

which can be deprotected to give a compound of formula

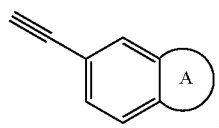
(E)

In a further preferred embodiment of the invention, the trialkylsilylacetylene is trimethylsilylacetylene.

In a further embodiment of the invention, the process for obtaining compounds of formula II or I comprises the steps of
cyclizing a compound of formula

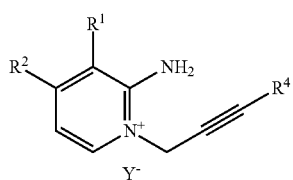
(C)

to obtain a compound of formula

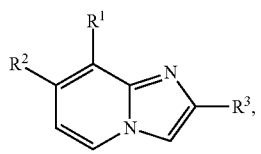
(J)

and, optionally,
further reacting compound of formula (J) to obtain a compound of formula

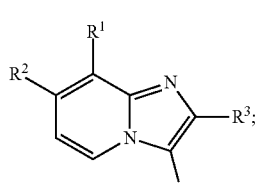
(K)

wherein

Y⁻ is Br⁻ or Cl⁻;

R¹ is selected from hydrogen, —C$_{1-3}$alkyl and halogen;

R² is selected from hydrogen, —C$_{1-3}$alkyl and halogen;

R³ is —CH$_2$—C$_{1-2}$alkyl;

R⁴ is selected from hydrogen and C$_{1-2}$alkyl

X is halogen.

In another embodiment, the process of the invention relates to compounds wherein R² is selected from —CH$_3$, —CH$_2$CH$_3$, —CH(CH$_3$)$_2$ and R$^a$ and R$^b$ are the same or different selected from —CH$_3$, —CH$_2$CH$_3$, —CH(CH)$_2$, —C(CH$_3$)$_4$, or —CH$_2$-phenyl or R$^a$ and R$^b$ together form pyrrolidine, piperidine or hexahydro-1H-azepine. Preferably, R$^a$ and R$^b$ are both —CH$_3$.

In another embodiment of the invention, the compounds of formula III can be further reacted with intermediates of formula J or K to obtain compounds of formula II.

In another embodiment of the invention, the compounds of formula III can be further reacted to obtain compounds of formula II and which can be further reacted to obtain compounds of formula I.

The process for obtaining compounds of formula II or III, in a preferred embodiment, further comprises the step of
deprotecting compounds of formula II to obtain a compound of formula

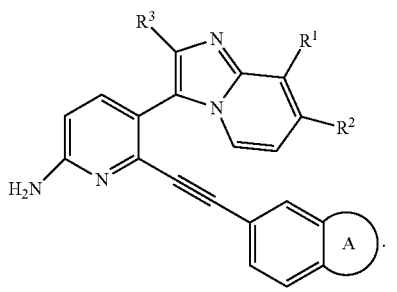

(M)

The process for obtaining compounds of formula II or III, in a preferred embodiment, further comprises the step of coupling a compound of formula M with 2-[methyl-[(2-methylpropan-2-yl)oxycarbonyl]amino]propanoic acid, wherein the 2-[methyl-[(2-methylpropan-2-yl)oxycarbonyl]amino]propanoic acid is racemic, S-2-[methyl-[(2-methylpropan-2-yl)oxycarbonyl]amino]propanoic acid or R-2-[methyl-[(2-methylpropan-2-yl)oxycarbonyl]amino]propanoic acid, to form a compound of formula

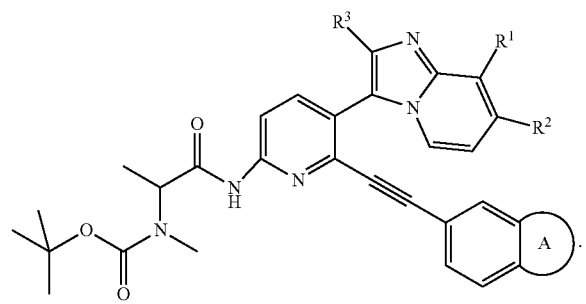

(N)

The process for obtaining compounds of formula II or III, in a preferred embodiment, further comprises the step of deprotecting the compounds of formula N to give a compound of formula I.

According to the invention, A is absent or is a 6-membered nitrogen containing heteroaryl, with one or two nitrogen atoms, preferably one, and optionally substituted with —CH$_3$.

According to the invention, R³ is selected from —C$_{1-3}$ alkyl, preferably —CH$_3$ and a 6-membered nitrogen containing heteroaryl, preferably pyridyl, which pyridyl is optionally substituted with —CH$_3$ or —O—CH$_3$, preferably —O—CH$_3$.

According to the invention, R² is selected from hydrogen or methyl.

According to the invention, R¹ is selected from hydrogen or methyl.

All compounds/intermediates specifically disclosed herein as such are an aspect of the invention.

Definitions

Terms that are not specifically defined here have the meanings that are apparent to the skilled man in the light of the overall disclosure and the context as a whole.

As used herein, the following definitions apply, unless stated otherwise.

In the groups, radicals, or moieties defined below, the number of carbon atoms is often specified preceding the group, for example, —C$_{1-5}$alkyl means an alkyl group or radical having 1 to 5 carbon atoms. In general, for groups comprising two or more subgroups, the first named subgroup is the radical attachment point, for example the substitutent —C$_{1-5}$alkyl-C$_{3-10}$cylcoalkyl, means a C$_{3-10}$cycloalkyl group which is bound to a C$_{1-5}$alkyl, the latter of which is bound to the core structure or to the group to which the substitutent is attached.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members.

The person skilled in the art will appreciate that substituent groups containing a nitrogen atom can also be indicated as amine or amino. Similarly, groups containing oxygen atom can also be indicated with -oxy, like for example alkoxy. Groups containing —C(O)— can also be indicated as carboxy; groups containing —NC(O)— can also be indicated as amide; groups containing —NC(O)N— can also be indicated as urea; groups containing —NS(O)$_2$— can also be indicated as sulfonamide.

Alkyl denotes monovalent, saturated hydrocarbon chains, which may be present in both linear and branched form. If an alkyl is substituted, the substitution may take place independently of one another, by mono- or polysubstitution in each case, on all the hydrogen-carrying carbon atoms.

The term "C$_{1-5}$-alkyl" includes for example methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$).

By the terms propyl, butyl, pentyl, etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy or $C_{x-y}$-alkoxy, wherein $C_{x-y}$-alkyloxy and $C_{x-y}$-alkoxy indicate the same group.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$, —$CH_2CH_3$ and —$CH_2CH_2$ or >$CHCH_3$ etc.

The term "$C_{1-4}$-alkylene" includes for example —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)(CH_2CH_3)$—.

Other examples of alkylene are methylene, ethylene, propylene, 1-methylethylene, butylene, 1-methylpropylene, 1.1-dimethylethylene, 1,2-dimethylethylene, pentylene, 1,1-dimethylpropylene, 2,2-dimethylpropylene, 1,2-dimethylpropylene, 1,3-dimethylpropylene, etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethyl-ethylene.

The above definition for alkylene also applies if alkylene is part of another group such as for example in HO—$C_{x-y}$-alkylenamino or $H_2N$—$C_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or $H_2N$—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl.

By the generic terms propynyl, butynyl, pentynyl, etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethyl-ethynylene.

The above definition for alkynylene also applies if alkynylene is part of another group, as in HO—$C_{x-y}$-alkynyleneamino or $H_2N$—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —Cl=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHFCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthalene), bicyclo[2.2.1]heptyl (norbornyl), bicyclo[4.1.0]heptyl (norcaranyl), bicyclo-[3.1.1]heptyl (pinanyl), spiro[2.5]octyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained.

The term cycloalkylene can thus be derived from the previously defined cycloalkyl.

Cycloalkylene, unlike cycloalkyl, is bivalent and requires two binding partners.

Formally, the second valency is obtained by removing a hydrogen atom from a cycloalkyl. Corresponding groups are for example cyclohexyl and

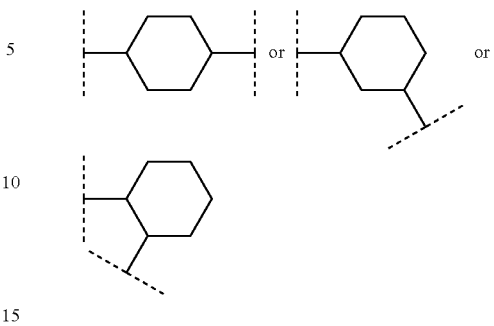

(cyclohexylene).

The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms.

Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norboma-2,5-dienyl), bicyclo[2.2.1]hept-2-enyl (norbomenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

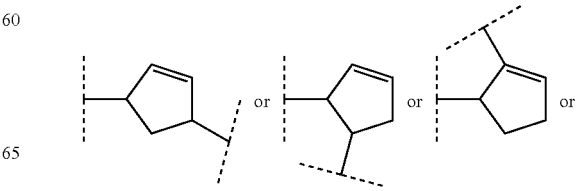

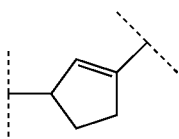

(cyclopentenylene) etc.

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes a mono-, bi- or tricyclic group with at least one aromatic carbocycle. Preferably it denotes a a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g.

phenyl and

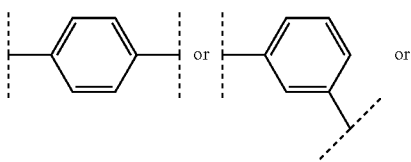

(o, m, p-phenylene), naphthyl and

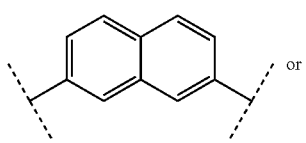

etc.

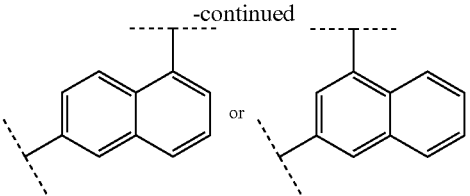

The above definition for arylene also applies when arylene is part of another group as in HO-aryleneamino or $H_2N$-aryleneoxy for example.

Heterocyclyl denotes ring systems, which are derived from the previously defined cycloalkyl, cycloalkenyl and aryl by replacing one or more of the groups —$CH_2$— independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO, sulphone —$SO_2$—; nitrogen→N-oxide).

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. Saturated and unsaturated, non aromatic, heterocyclyl are also defined as heterocycloalkyl. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. When the heterocyclyl has a nitrogen atom, the preferred position to bind the heterocyclyl substituent to the molecule is the nitrogen atom.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]-octyl, 3,9-diaza-bicyclo[4.2.1]nonyl, 2,6-diaza-bicyclo[3.2.2]nonyl, 1,4-dioxa-spiro[4.5]decyl, 1-oxa-3.8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2.8-diaza-spiro[4.5]decyl etc.
Further examples are the structures illustrated below, which may be attached via each hydrogen-carrying atom (exchanged for hydrogen):
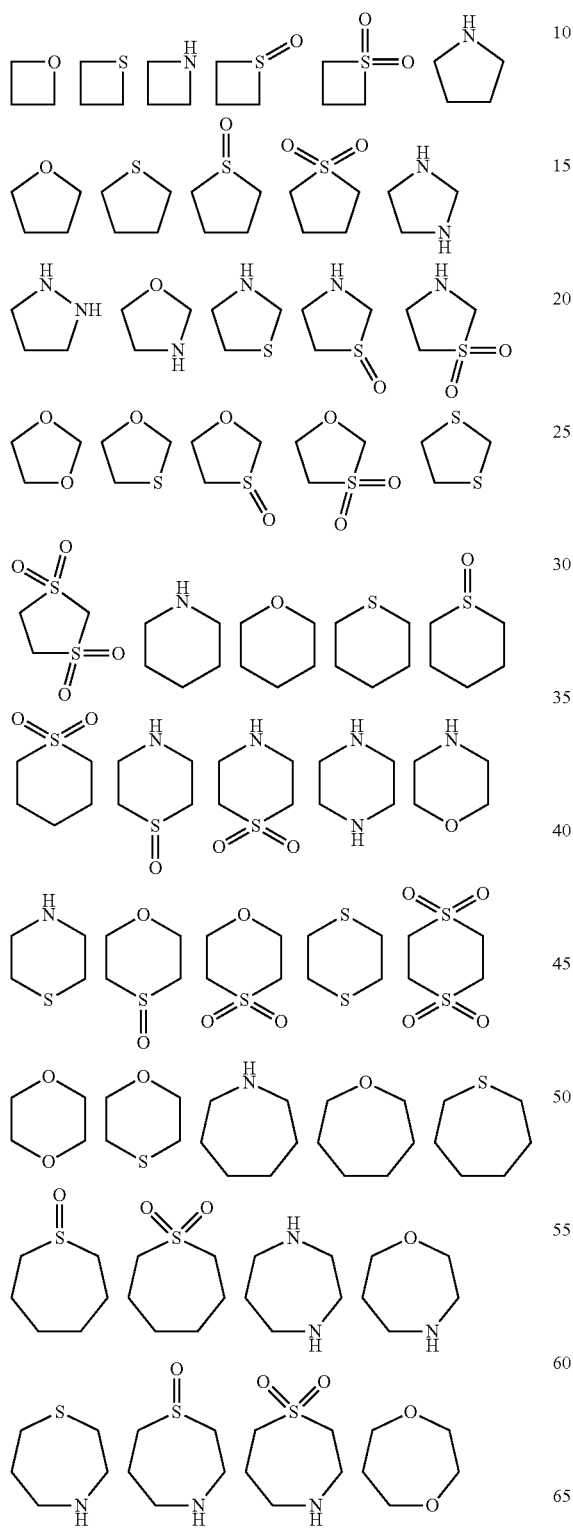
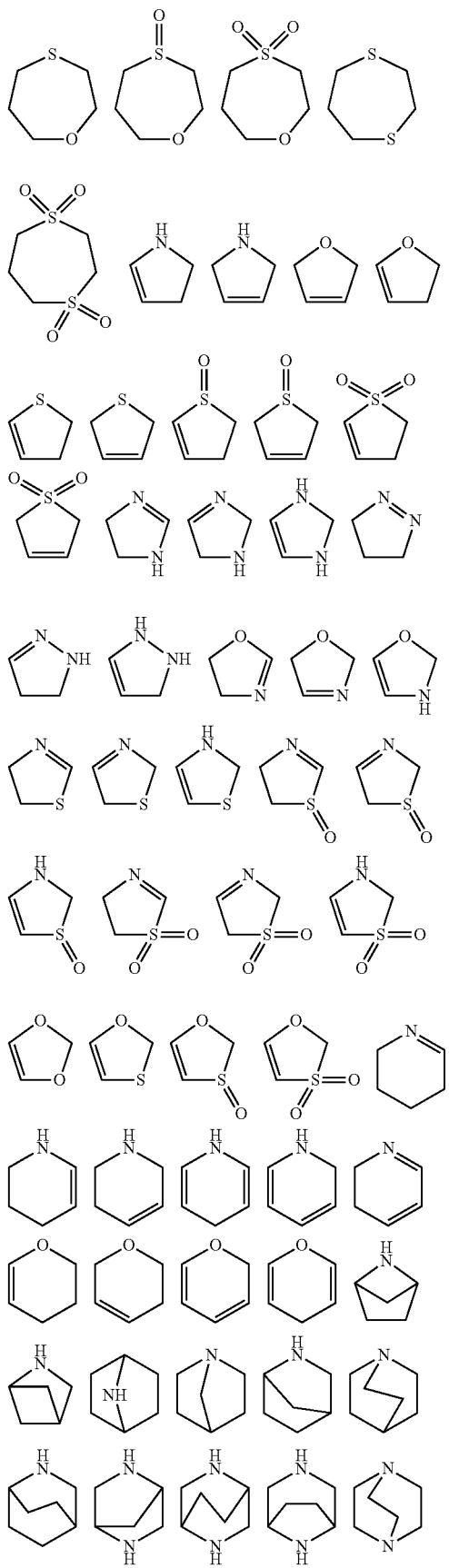

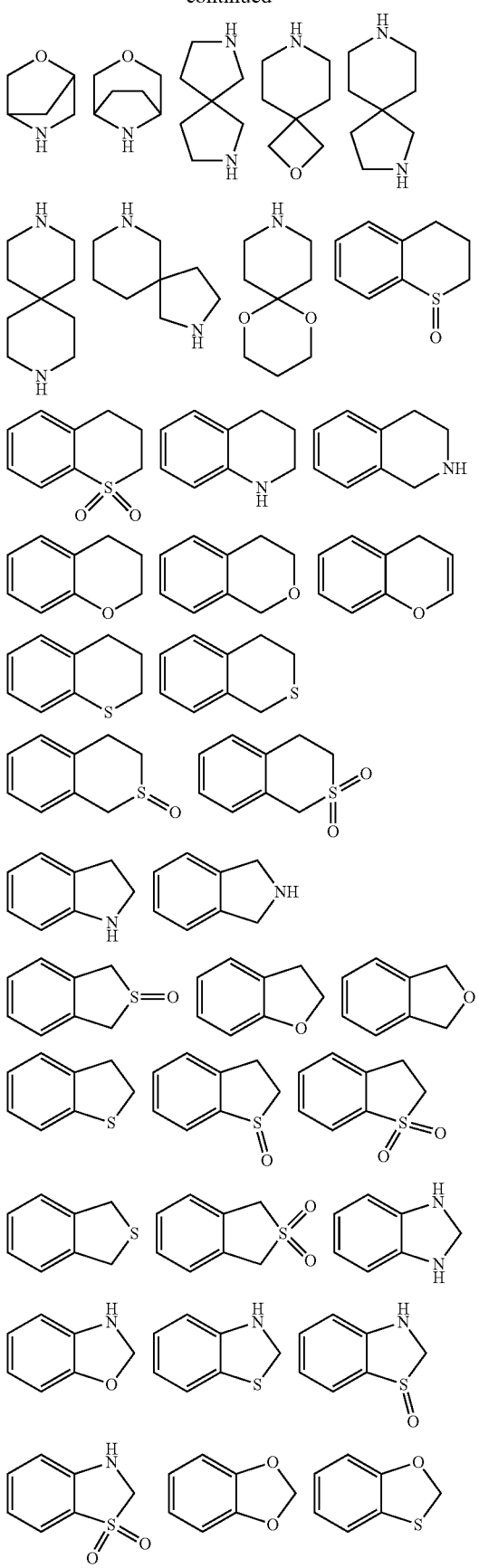
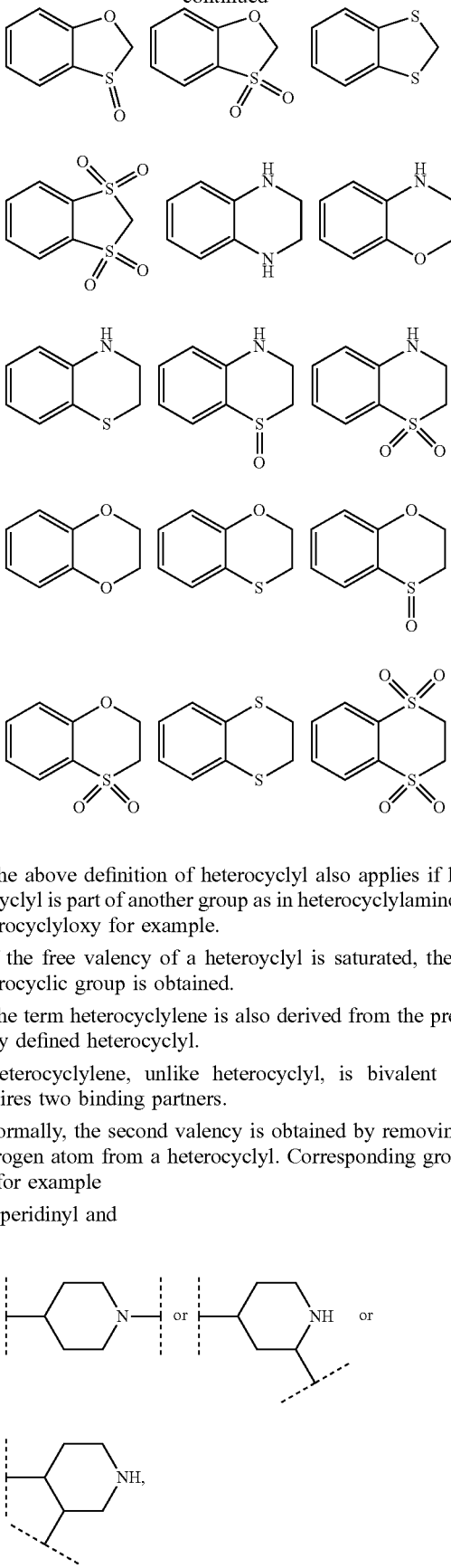

The above definition of heterocyclyl also applies if heterocyclyl is part of another group as in heterocyclylamino or heterocyclyloxy for example.

If the free valency of a heteroyclyl is saturated, then a heterocyclic group is obtained.

The term heterocyclylene is also derived from the previously defined heterocyclyl.

Heterocyclylene, unlike heterocyclyl, is bivalent and requires two binding partners.

Formally, the second valency is obtained by removing a hydrogen atom from a heterocyclyl. Corresponding groups are for example piperidinyl and

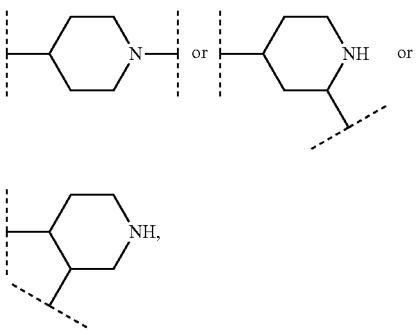

2,3-dihydro-1H-pyrrolyl and

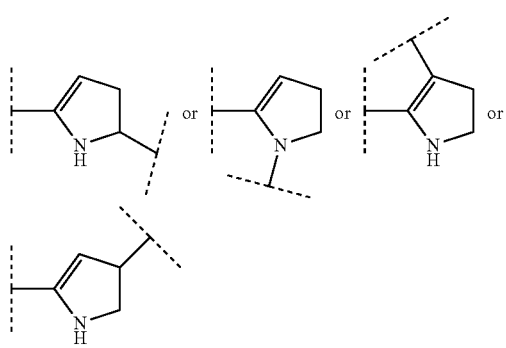

etc.

The above definition of heterocyclylene also applies if heterocyclylene is part of another group as in HO-heterocyclyleneamino or H₂N-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen. Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

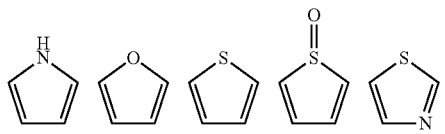

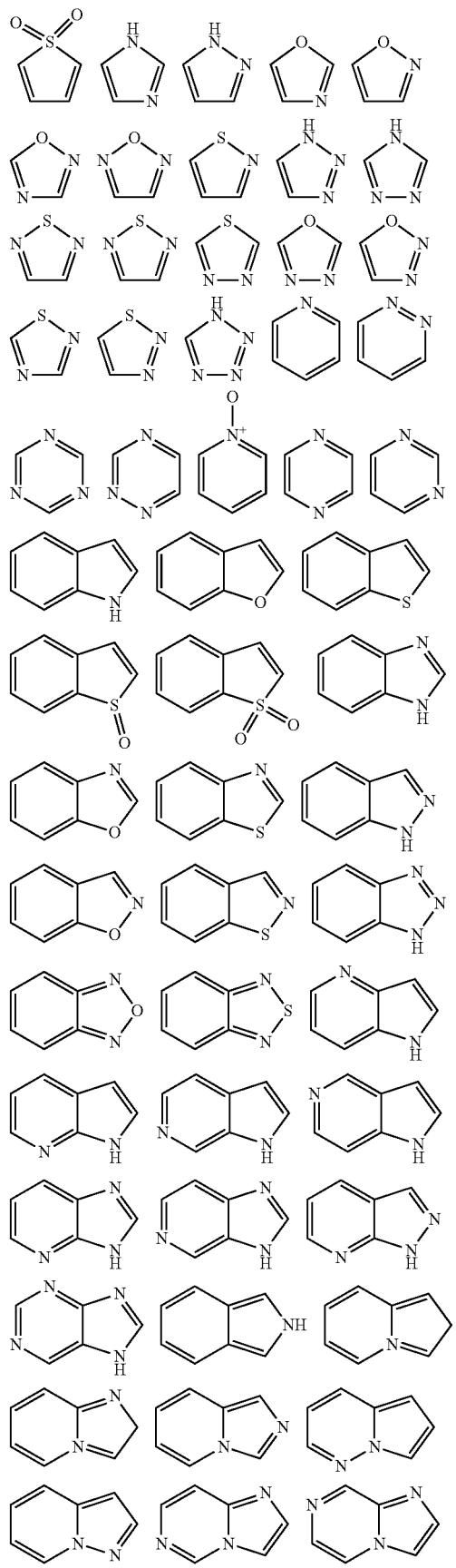

-continued

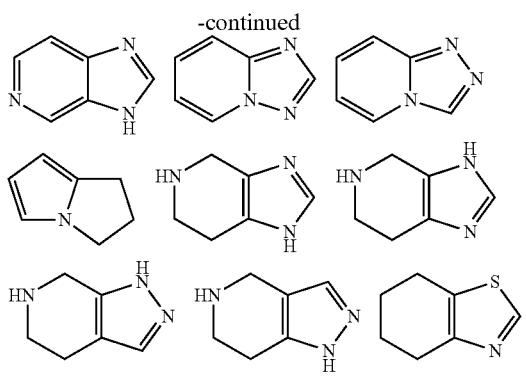

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and

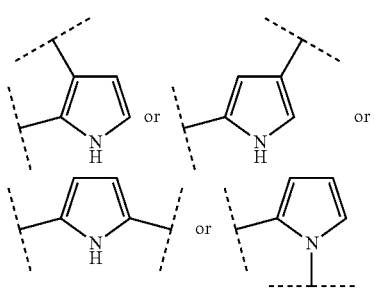

etc.

The above definition of heteroarylene also applies when heteroarylene is part of another group as in HO-heteroaryleneamino or $H_2N$-heteroaryleneoxy, for example.

The bivalent groups mentioned above (alkylene, alkenylene, alkynylene etc.) may also be part of composite groups (e.g. $H_2N$—$C_{1-4}$alkylene- or HO—$C_{1-4}$alkylene-). In this case one of the valencies is saturated by the attached group (here: —$NH_2$, —OH), so that a composite group of this kind written in this way is only a monovalent substituent over all.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =$N_2$ or the like, may only be substituted at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —$CH_2$— or sulphur atoms of a ring system.

List of Abbreviations

ACN, $CH_3CN$ acetonitrile
Boc tert.butoxy carbonyl
DCM dichloromethane
DIPEA diisopropylethyl amine
DMAP dimethyl-pyridin-4-yl-amine
DMF N,N-dimethylformamide
DMSO dimethylsulphoxide
DMI dimethylimidazolidinone
EtOAc or EA ethyl acetate
HMPA Hexamethylphosphoramide
h hour(s)
HATU  N-[(dimethylamino)-(1H-1,2,3-triazolo[4,5-b]pyridin-1-yl)-methylene]-N-methylmethan-aminium hexafluorophosphate N-oxide
HPLC high performance liquid chromatography
KOAc potassium acetate
M Molar
Min minute(s)
mL Millilitre
MS (ESI) mass spectrometry (electrospray ionization)
N Normal
NMR nuclear resonance spectroscopy
NMP N-Methyl-2-pyrrolidone
PPh3 triphenylphosphine
DIBAL diisobutylaluminium hydride
RP reversed phase
Rpm rounds per minute
RT or rt room temperature
nBuOH n-Butanol
TBME tert.butyl methyl ether
TEA triethylamine
tert tertiary
TFA trifluoroacetic acid
THF tetrahydrofuran
TPPA tris(N,N-tetramethylene)phosphoric acid triamide
tR retention time [min]
TRIS tris(hydroxymethyl)aminomethane
wt % weight percent
sat. Saturated General Description of the Method for the Preparation of Intermediates of Formula I, II and III According to the Invention The process for the synthesis of compounds I, II and III is represented in Scheme V and described in more details herein below.

Scheme II

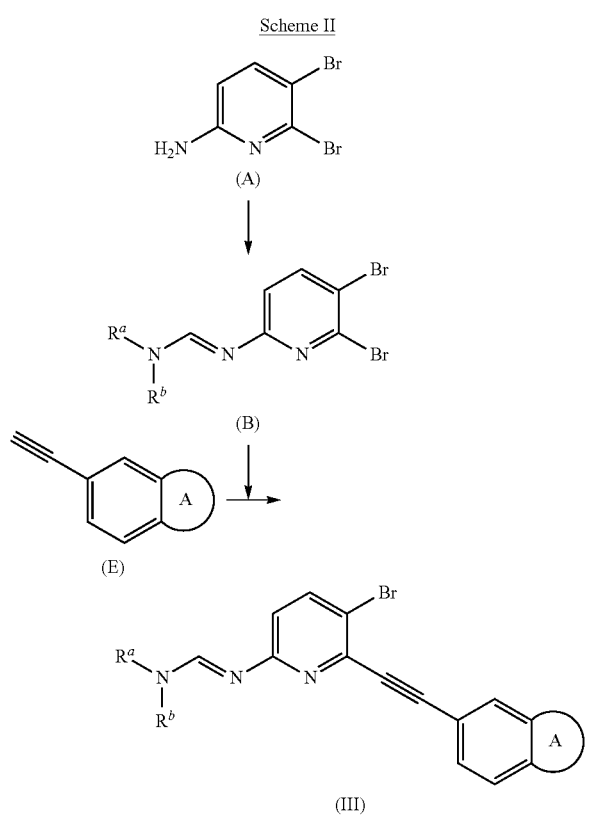

As illustrated in the synthesis scheme II, the process of the invention comprises the steps of reacting an alkyne of the type E via a Sonogashira cross coupling.

The reaction of alkynes of the type E with the amidine B is carried out in the presence of a palladium source, a copper(I) salt, a base and optionally of (L)-ascorbic acid and of a ligand. Preferably, the palladium source is a stable palladium complex such as bis(triphenylphosphinepalladium)dichloride. Preferred ligand is a phosphine ligand such as triphenylphosphine. As copper(I) salt is preferably used copper iodide and the preferred base is an amine such as diisopropylamine, diisopropylethylamine or triethylamine. The reaction can be carried out in alcohols, acetonitrile, ethers or toluene, preferably in toluene, at temperatures of 20-100° C., preferably at 50-70° C. The reaction products III are isolated per crystallization or chromatography.

General Description of the Method for the Preparation of Intermediates of Formula (E) According to the Invention The compounds according to the invention are prepared by the methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis. Unless otherwise specified, the substituents of the following reaction schemes are as defined in the description and claims.

In a further embodiment of the invention, the process for the synthesis of compounds of formula I, II or III comprises the following steps for the synthesis of compounds of formula E.

In a preferred embodiment of the invention, a compound of formula

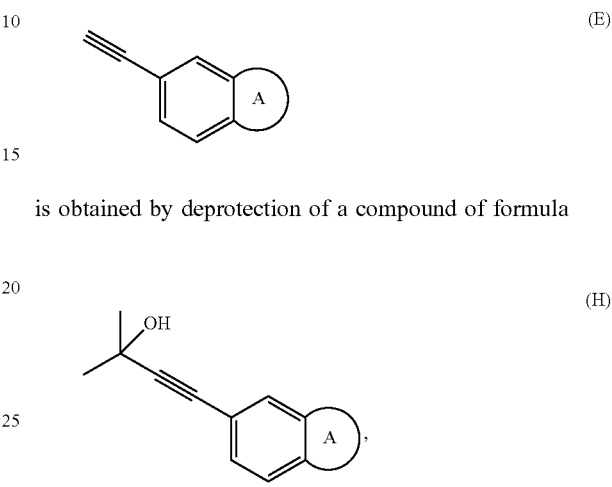

is obtained by deprotection of a compound of formula wherein

A is absent or is a 6-membered nitrogen containing heteroaryl optionally substituted with a —$C_{1-3}$alkyl group.

Preferably, deprotection is obtained in basic conditions. Thus, the deprotection of alkyne H to give E is carried out in the presence of a base such as NaH, KOH or $K_3PO_4$ or combinations thereof in an organic solvent such as toluene, xylene, 2-methyltetrahydrofuran or tetrahydrofuran at 40° C. to 100° C. More preferably the reaction is carried out in toluene at 55° C. The product isolation is carried out as described below or used directly in solution in the next step.

Scheme III

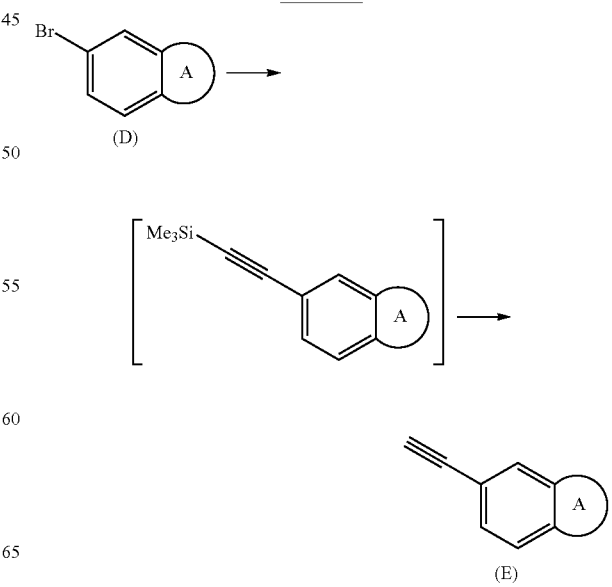

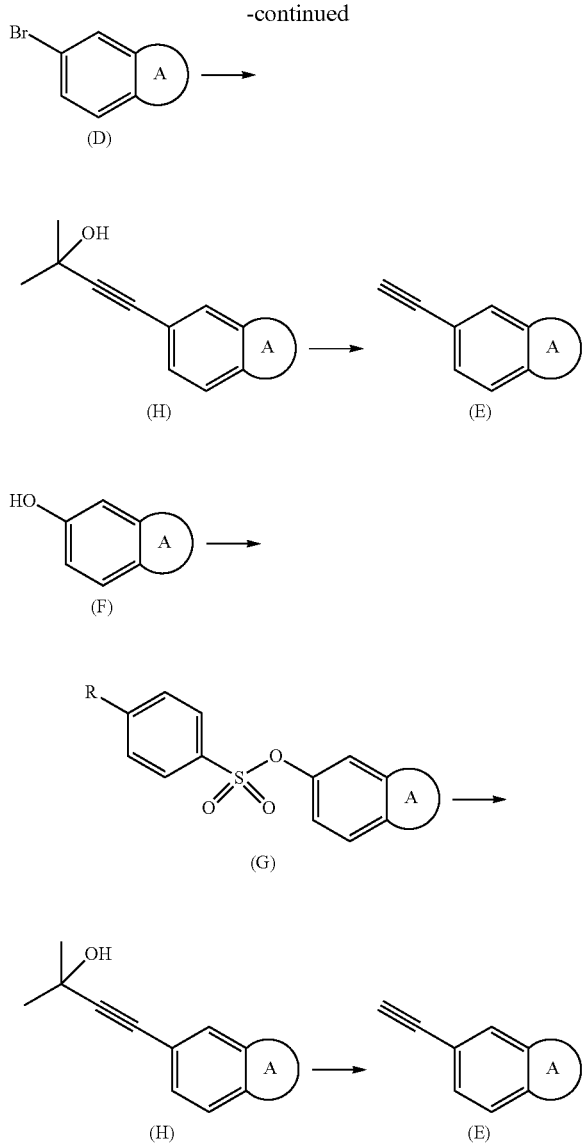

Preparation of Compounds E 6-ethynyl-derivatives E may be synthesized in accordance with the processes shown in the synthesis Scheme III.

For example, the 6-ethynyl-quinoline E1 is obtained by a two-step procedure consisting of an Sonogashira cross coupling with ethynyltrimethylsilane, followed by desilylation.

Preparation of Compounds G and H

Alkynes of the type H are obtained by the two-step procedure shown in the synthesis Scheme III. Thus, after converting the phenol moiety in F into a sulfonic acid ester such as a tosylate or a benzensulfonate G, a Sonogashira cross coupling with 2-methyl-3-butyn-2-ol leads to H. The sulfonic acid ester G is preferably prepared by reaction of the corresponding phenol F with toluenesulfonic acid chloride or benzensulfonic acid chloride in the presence of a base, preferably a tertiary amine base, preferably triethylamine and diisopropylethylamine. The reaction is preferably carried out in an aprotic solvent such as dichloromethane, DMF, THF, acetonitrile or acetone at a temperature of 20-100° C. More preferably the reaction is carried out in acetone at a temperature of 50-60° C. The product G can be isolated by crystallization or chromatography.

The reaction of the sulfonic acid ester with 2-methyl-3-butyn-2-ol is carried out in the presence of a palladium source, a ligand and a base. As palladium source is used preferably a stable palladium salt such as palladium acetate. As ligand is preferably used a phosphine ligand such as 2-dicyclohexylphosphino-2',6'-diisopropoxy-1,1'-biphenyl ("RuPhos"). A carbonate base such as potassium carbonate is preferably used as the base. The reaction can be carried out in alcohols, acetonitrile, ethers, toluene or water or mixtures of these at 40° C. to 100° C. More preferably the reaction is carried out in 2-propanol/water mixtures at 75° C. to 85° C. Subsequently, the solvent is replaced by a nonpolar solvent, preferably toluene, and the inorganic compounds are removed by aqueous washes. The alkynes H can be isolated by crystallization or directly used in solution in the subsequent reaction step after an extractive work up and concentration of the organic extracts.

Compounds III are obtained from alkynes of the type H by a two-step procedure consisting of a deprotection step followed by a Sonogashira cross coupling as illustrated in the synthesis Scheme II.

The deprotection reaction to give alkynes E occurs by treatment of alkynes H with a base. Preferably, an inorganic base such as an alkali hydroxide, carbonate or phosphate is employed and more preferably a mixture of potassium hydroxide and potassium phosphate is utilized. The reaction is carried out in aprotic solvents such as toluene, THF, or acetonitrile, preferably toluene at temperatures of 25-120° C., preferably 90-110° C. At the end of the deprotection step inorganic compounds are removed by filtration or aqueous work up and the organic phase is then used directly in the next reaction step.

The subsequent Sonogashira cross coupling is carried out employing the same reaction conditions described above.

Alternatively, alkynes of the type H may be prepared from (heterocyclic) bromides of the type D as shown in the synthesis Scheme II. Thus, reaction of bromides D with 2-methyl-3-butyn-2-ol is carried out in the presence of a palladium source, a ligand, a copper(I) salt and a base. As palladium source is used preferably a stable palladium salt such as bis(triphenylphosphine)palladium dichloride. Preferred ligand is a phosphine ligand such as triphenylphosphine. As copper(I) salt is preferably used copper iodide and the preferred base is an amine such as triethylamine, diisopropylamine, diisopropylethylamine. The reaction can be carried out in alcohols, acetonitrile, ethers, toluene or water or mixtures of these at 40° C. to 100° C. More preferably the reaction is carried out in 2-methyltetrahydrofuran at 80° C. The product isolation is carried out as described above or crystallized from an appropriate solvent such as iPrOAc.

Scheme IV
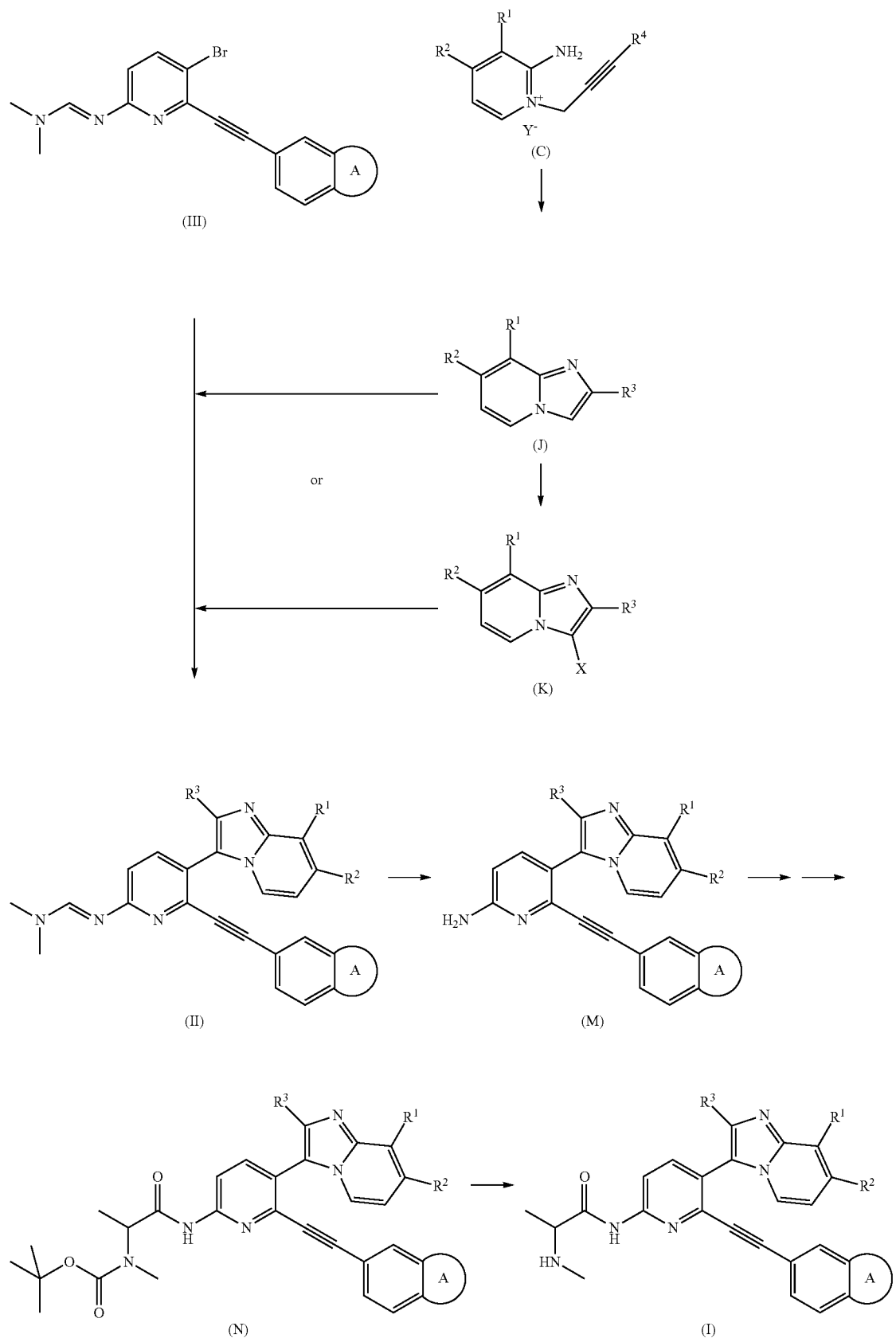

In another embodiment of the invention, halogenoimidazopyridines K are obtained from pyridinium salts of the type C by a cyclization to imidazo[1,2-a]pyridines J followed by a halogenation step as shown in synthesis Scheme IV.

The cyclization may be mediated by an appropriate base such as a strong inorganic base, preferably sodium hydroxide, and is carried out in a protic or aprotic solvent such as acetonitrile, methanol and THF, preferably in methanol. The reaction is maintained at a temperature of about 5° C. to 60° C. and preferably at 15° C. to 35° C. The halogenation agent (e.g. N-iodosuccinimide) is then added at ambient temperature. The reaction products K are isolated per crystallization or chromatography.

Scheme V

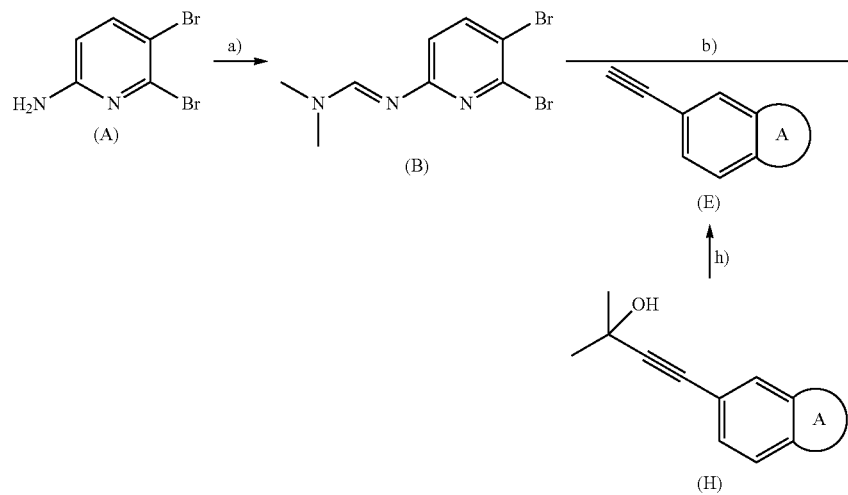

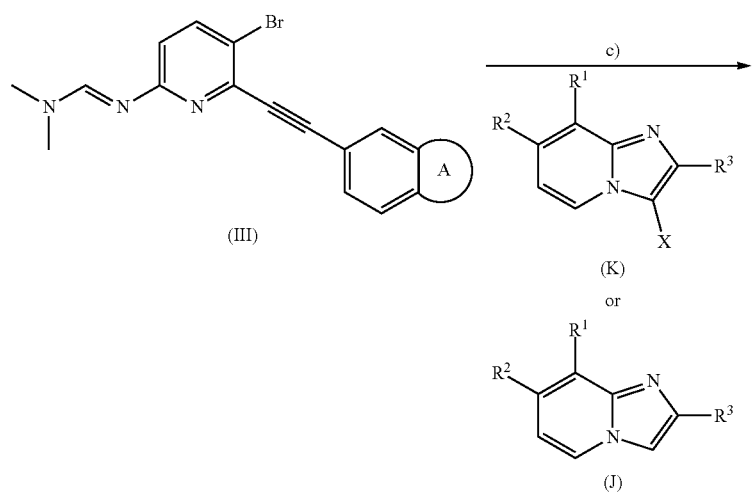

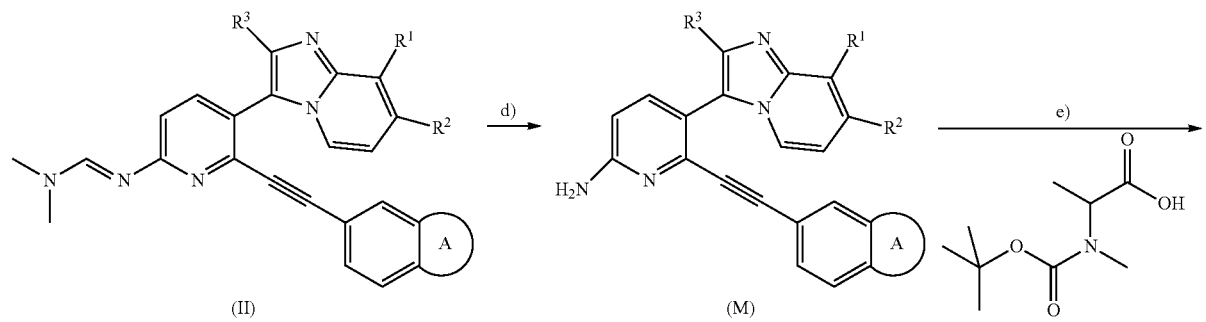

-continued

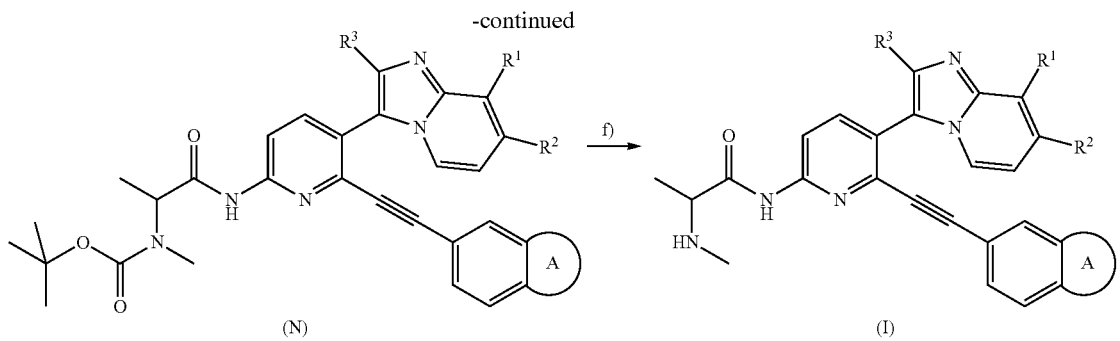

Preparation of B1: N'-(5,6-Dibromo-pyridin-2-yl)-N,N-dimethyl-formamidine

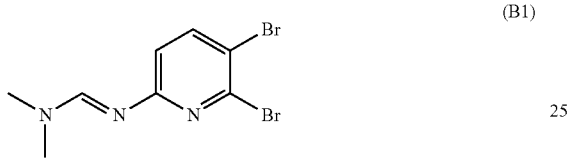

A mixture of 5,6-dibromo-pyridin-2-ylamine (10 kg, 39.7 mol) A and methylcyclohexane (40 L) is heated to 65° C. At this temperature is added N,N-dimethylformamide dimethyl acetal (4.97 kg, 41.7 mol) over a period of 30 min rinsing with methylcyclohexane (10 L). The reaction mixture is heated to 100° C. for 1 h or until the reaction is complete while removing 10 L of solvent under reduced pressure. Then, methylcyclohexane (20 L) is added and the mixture is cooled to about 60-55° C. Crystallization is initiated by addition of seeding crystals and the resulting suspension is cooled to 20° C. over a period of 4 h and then stirred for additional 15 min at this temperature. The title product B is isolated by filtration, washed with methylcyclohexane (2×15 L) and dried under vacuum at 50° C. Yield 80%. MS (ESI+) m/z=306/308/310 [M+H]$^+$.

Preparation of D1: 6-Bromo-1-methyl-isoquinoline

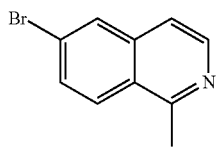

6-Bromo-1-chloro-isoquinoline (60.0 g, 0.24 mol) is combined with Me-THF (270 mL) and tetramethylethylendiamine (18.7 mL, 0.12 mol) is added, rinsing with Me-THF (5 mL). Iron(III)acetylacetonate (437 mg, 1.24 mmol) is added, rinsing with Me-THF (5 mL). The resulting mixture is cooled to 0° C. and methyl magnesium chloride, 3.0 M in THF (86.6 mL, 0.26 mol) is added at 0-2° C. in 1 h, rinsing with Me-THF (20 mL). After 1.5 h at 0° C. additional methyl magnesium chloride solution is added (16.5 mL, 0.05 mol) in 0.5 h at the same temperature, rinsing with Me-THF (5 mL). After stirring at 0° C. for 0.5 h a 5% aqueous solution of citric acid (300 mL) is added at 0-20° C. and the organic phase is separated. The organic phase is washed with 5% aqueous solution of citric acid (210 mL), then with brine (210 mL) and finally dried over sodium sulfate. The title product D1 is obtained by evaporation of the solvent. Yield 80%. MS (ESI$^+$) m/z=222/224 [M+H]$^+$.

Preparation of E1: 6-Ethynyl-quinoline hydrochloride

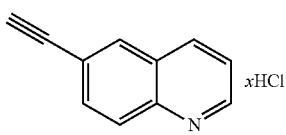

10.00 kg (48.06 mol) of 6-bromochinoline are combined with 12.16 kg (120.16 mol) of dry triethylamine and 2-methyltetrahydrofurane (40.0 L) and the mixture is degassed. 337.4 g (0.48 mol) bis(triphenylphosphine)palladium(II) dichloride, 183.1 g (0.96 mol) copper(I) iodide and 252.1 g (0.96 mol) triphenylphosphine are added. The reaction mixture is degassed again and set to 55° C. 6.54 kg (67.29 mol) of trimethylsilylacetylene dissolved in degassed 2-methyltetrahydrofurane (10.0 L) are added. After complete reaction a mixture of 9.00 kg (132.17 mol) conc. ammonia in purified water (30.0 L) is added and the reaction mixture is filtered over a 2.50 kg charcoal cartridge, rinsing with purified water (10.0 L) and 2-methyltetrahydrofurane (10.0 L). The organic phase is separated and washed with a mixture of 9.00 kg (132.17 mol) conc. ammonia and purified water (40.0 L). The organic phase is concentrated under vacuum and abs. ethanol (20.0 L) are added. After cooling to 20° C. the resulting solution is added to a cold (7° C.) mixture of 0.38 kg (4.81 mol) sodium hydroxide, 50 wt. % aqueous solution, purified water (0.50 L) and abs. ethanol (20.0 L), rinsing with abs. ethanol (5.0 L). After complete reaction (HPLC) a mixture of 5.65 kg (57.68 mol) 10 N hydrochloric acid in ethanol and abs. ethanol (5.0 L) is added, rinsing with abs. ethanol (5.0 L). The resulting suspension is stirred 1 h at 20° C. and the product E1 is recovered by centrifugation, washed twice with 10.0 L abs ethanol and dried at 50° C. under vacuum.

Yield: 89%. MS (ESI+) m/z=154 [M+H]$^+$

The following compounds E2 and E3 can be prepared under analogous conditions (analogous conditions include potential deviations from the disclosed conditions in terms of, e.g., solvent, reaction conditions or purification which the skilled artisan is familiar with and takes into account):

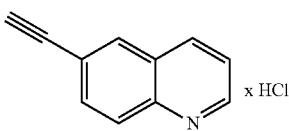

E1

MS (ESI+) m/z = 154 [M+H]+

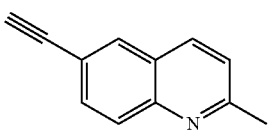

E2

MS (ESI+) m/z = 168 [M+H]+

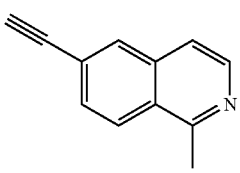

E3

MS (ESI+) m/z = 168 [M+H]+

Preparation of G1: Toluene-4-sulfonic acid 1-methyl-isoquinolin-6-yl ester

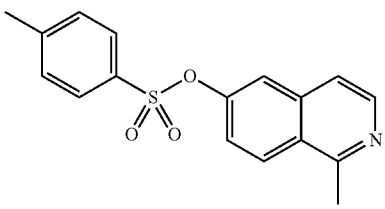 [SMILES: Cc1ccc(S(=O)(=O)Oc2ccc3c(C)nccc3c2)cc1]

A stirred mixture of 1-methyl-isoquinolin-6-ol hydrobromide (1.81 kg, 7.53 mol), p-toluenesulfonyl chloride (144 g, 7.53 mol) and acetone (18 L) is heated to reflux. At this temperature is added triethylamine (2.61 L, 18.8 mol) and after being stirred at reflux for 30 min or until complete conversion the reaction mixture is cooled to room temperature and water (9.0 L) is added. Crystallization may be initiated by addition of seeding crystals. To the resulting suspension is added water (18 L) over a period of 30 min. The solid is recovered by filtration, washed with a mixture of acetone/water 2/8 (10 L) and water (5.0 L) and dried to afford the title compound G1. Yield: 87%. MS (ESI+) m/z=314 [M+H]+.

The 1-methyl-isoquinolin-6-ol may be synthesized following literature procedures (*Journal of Organic Chemistry USSR*, English Translation, 1992, 28, 642-646).

The following compound G2 is synthetized analogously (analogous conditions include potential deviations from the disclosed conditions in terms of, e.g., solvent, reaction conditions or purification which the skilled artisan is familiar with and takes into account).

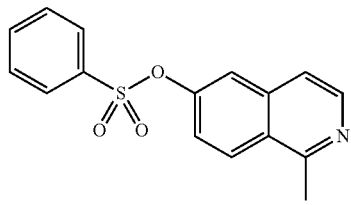

G2

MS (ESI)+ m/z = 300 [M+H]+

Preparation of H1: 2-Methyl-4-(1-methyl-isoquinolin-6-yl)-but-3-yn-2-ol

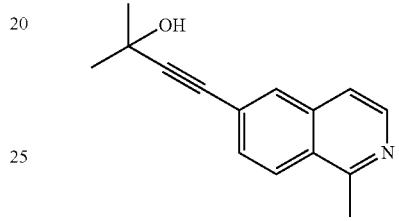

A mixture of toluene-4-sulfonic acid 1-methyl-isoquinolin-6-yl ester G1 (1.74 kg, 5.54 mol), 2-methyl-3-butyn-2-ol (810 mL, 8.31 mol) and 2-propanol (8.5 L) is degassed and heated to reflux under an atmosphere of argon. To this mixture is added a degassed solution of $K_2CO_3$ (1.00 kg, 7.20 mmol) in water (8.5 L), palladium acetate (12.4 g, 55.4 mmol) and 2-dicyclohexylphosphino-2',6'-di-propoxy-1,1'-bisphenyl (RuPhos) (53.3 g, 111 mmol). The resulting mixture is heated to reflux for 3 h or until the reaction is complete. Then, 8.5 L of solvent is distilled off and toluene (12 L) is added. Another 3 L of solvent is removed in vacuo and the mixture is maintained at 60° C. The organic layer is separated, washed with water (10 L) and concentrated to afford crude product H1, which is used without further purification. Yield: Quant. MS (ESI+) m/z=226 [M+H]+.

Preparation of Compounds III

Preparation of III-1: N'-(5-Bromo-6-quinolin-6-ylethynyl-pyridin-2-yl)-N,N-dimethyl-formamidine

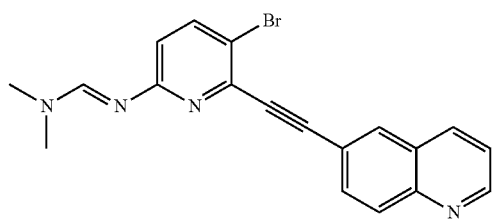 [SMILES: CN(C)/C=N/c1ccc(Br)c(C#Cc2ccc3ncccc3c2)n1]

3.67 kg (19.35 mol) of compound E1 and 5.40 kg (32.57 mol) of N'-(5,6-dibromo-pyridin-2-yl)-N,N-dimethyl-formamidine B1 are suspended in toluene (22.0 L). 8.95 kg (87.95 mol) diisopropylamine are added at 20-30° C. rinsing with 5.0 L toluene and the reaction mixture is degassed. 92.3 g (0.18 mol) bis(triphenylphosphine)palladium(II) dichloride, 67.0 g (0.35 mol) copper(I) iodide and 92.3 g (0.35 mol) triphenylphosphine are added. The reaction mixture is degassed again and set to 50° C. After 2 h or when reaction is complete a mixture of 4.9 kg conc. ammonia in purified water (11.0 L) is added, rinsing with water (5.0 L) and the reaction mixture is cooled to 40° C. and filtered over a Celite cartridge, rinsing with toluene (11.0 L). The organic phase is separated diluted with toluene (5.0 L) and washed again with a mixture of 4.9 kg of conc. ammonia and purified water (16.0 L). The organic phase is concentrated under vacuum. 33.0 L solvent are removed and n-heptane (8.0 L) is added. Crystallization may be initiated by addition of seeding crystals and the mixture is cooled to 20° C. in 2-3 h. During the cooling phase additional n-heptane (8.5 L) is added. After 1 h stirring at 20° C. the product III-1 is recovered by centrifugation, washed with a mixture of n-heptane (9.0 L) and toluene (6.0 L) and dried at 50° C. under vacuum.

Yield 87% MS (ESI$^+$) m/z=379/381 [M+H]$^+$

The following compounds III-2 to III-4 are prepared under analogous conditions starting from B and the corresponding alkyne E (analogous conditions include potential deviations from the disclosed conditions in terms of, e.g., solvent, reaction conditions or purification which the skilled artisan is familiar with and takes into account).

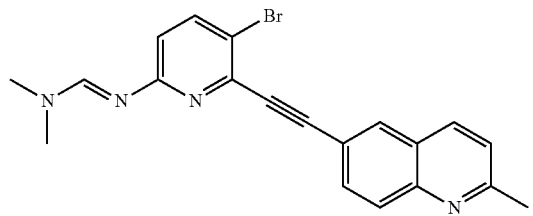

III-2

MS (ESI)$^+$ m/z = 379/381 [M+H]$^+$

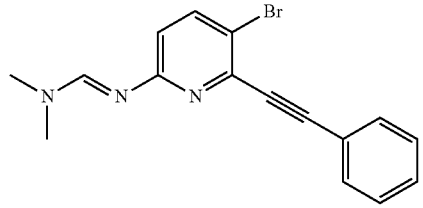

III-3

MS (ESI)$^+$ m/z = 393/395 [M+H]$^+$

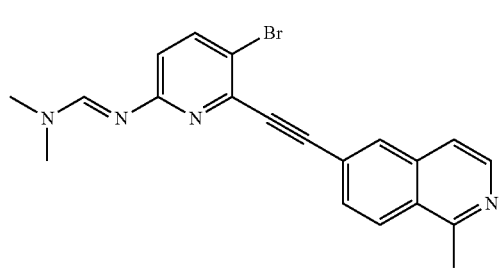 [SMILES: Cc1nccc2cc(C#Cc3nc(/N=C/N(C)C)ccc3Br)ccc12]

III-4

MS (ESI)$^+$ m/z = 328/330 [M+H]$^+$

Preparation of III-4: N'-[5-Bromo-6-(1-methyl-iso-quinolin-6-ylethynyl)-pyridin-2-yl]-N,N-dimethyl-formamidine

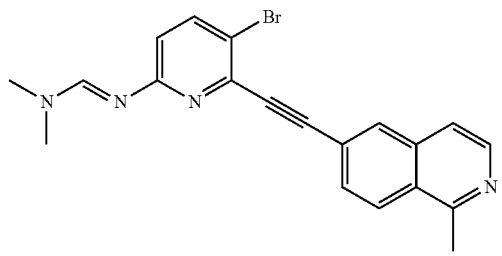

Under argon atmosphere a mixture of KOH (146 g, 2.22 mol), K$_3$PO$_4$ (470 g, 2.22 mol) and toluene (7.0 L) is heated to 55° C. At this temperature is added a solution of 2-methyl-4-(1-methyl-isoquinolin-6-yl)-but-3-yn-2-ol H1 (1.74 kg, 5.54 mol) in toluene (3.5 L) obtained as described above and the resulting mixture is stirred at 55° C. for 15 min. At this temperature, 3.5 L of solvent is distilled off over the course of 1 h under reduced pressure and toluene (5.0 L) is added subsequently. Then, 8.5 L of solvent is distilled off during 1 h and toluene (5.0 L) is added. After consumption of starting material, 11.5 L of solvent is removed under reduced pressure, the mixture containing the alkyne E3 is cooled to 15° C., filtered over a pad of activated carbon rinsing with toluene (5.0 L). 15 L of solvent is removed under reduced pressure, N-(5,6-dibromo-pyridin-2-yl)-N,N-dimethyl-formamidine B1 (1.53 kg, 4.99 mol) and diisopropylamine (3.9 L, 27.7 mol) is added and the mixture was degassed. To this mixture is added bis(triphenylphosphino)palladium(II) chloride (39.0 g, 55.4 mmol), copper iodide (21.0 g, 1.60 mmol) and triphenylphosphine (14.5 g, 55.4 mmol). After stirring at 55° C. for 1.5 h or until complete conversion, water (7.0 L) and a 25% aq. ammonia solution (1.3 L) is added and the phases are separated. The organic layer is washed with a mixture of water (7.0 L) and a 25% aq. ammonia solution (1.3 L) and concentrated. The residue is diluted with methylcyclohexane (15 L), heated to reflux and after removal of 2 L of solvent cooled to 40° C. The resulting precipitate is recovered by filtration off to afford the title compound III-4. Yield: 66%. MS (ESI$^+$) m/z=393/395 [M+H]$^+$ If necessary, alkyne E3 may be isolated before performing the Sonogashira reaction. MS (ESI$^+$) m/z=168 [M+H]$^+$.

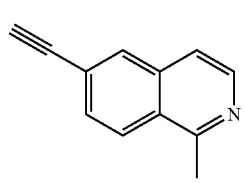

E3

The intermediates III can be further functionalized by performing cross coupling reactions at the 5-position bearing the halogen atom with the appropriate imidazo[1,2-a]pyridine as shown in the synthesis Scheme V.

Preparation of Compounds K

Preparation of compound K1:
3-Iodo-2-methyl-imidazo[1,2-a]pyridine

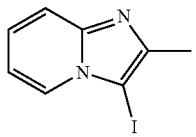

2-Amino-1-(prop-2-yn-1-yl)pyridin-1-ium bromide C1 (150.0 g, 0.66 mol) is suspended in methanol (600 mL) and 4 N sodium hydroxide aq. solution (530.0 mL, 2.12 mol) is added in 30 min at 15-35° C. After stirring for 2 h at 20° C., N-iodosuccinimide (175.0 g, 0.78 mol) is added in portions to the resulting solution of 2-methylimidazo[1,2-a]pyridine J1 at 21-24° C. After 2.5 h, purified water (600 mL) is added in 30 min and after stirring overnight at 20° C. the product K1 is isolated by filtration, washed with water (360 mL) and dried at 50° C. under vacuum. Yield: 82%. MS (ESI$^+$) m/z=259 [M+H]$^+$.

Alternatively, the 2-methylimidazo[1,2-a]pyridine J1 is isolated before the addition of N-iodosuccinimide in 98% yield. HPLC-MS: M+H=133

Preparation of Compounds II and M

As shown in synthesis scheme V upon a cross coupling reaction between bromides III and imidazo[1,2-a]pyridines J or 3-halogeno imidazo[1,2-a]pyridines K compounds II are obtained. Compounds M are prepared by cleavage of the N,N-dimethylformamidine protecting group.

The 3-halogeno-imidazo[1,2-a]pyridines K can be metallated and subsequently cross coupled with III in the presence of a palladium source, a ligand and optionally of other additives. The halogen atom is preferably iodine. The metallation step can be carried out with an appropriate metallating agent such as isopropylmagnesium chloride or isopropylmagnesium chloride lithium chloride complex solutions followed by a treatment with a transmetallating agent such as ZnBr$_2$ or ZnCl$_2$. The metallation/transmetallation sequence reaction is preferably carried out in ethers (e.g. Me-THF or THF) or in polar aprotic solvents (e.g. NMP, DMI, HMPA, tris(N,N-tetramethylene)phosphoric acid triamide: TPPA) or mixtures of these at −20° C. to 60° C. More preferably the metallation/transmetallation sequence is carried out in THF or THF/TPPA mixtures at 0-20° C. The solution of the metallated imidazo[1,2-a]pyridine is then combined with a solution of III and cross coupled in the presence of a palladium catalyst and a ligand.

As palladium source is used preferably a stable palladium salt or complex such as bis(dibenzylideneacetone)palladium, tri(dibenzylideneacetone)dipalladium, Pd(OAc)$_2$, Pd(OPiv)$_2$, tetrakis(triphenylphosphine)palladium, bis(triphenylphosphinepalladium)-dichloride, Preferably bis(dibenzylideneacetone)palladium.

As a ligand a phosphine ligand is used such as triphenylphosphine, tBuXPhos, BrettPhos, RuPhos, SPhos, di(1-adamantyl)-n-butylphosphine. Preferred ligand is RuPhos. The cross coupling step is carried out at a temperature of 20-80° C. and preferably at 40-65° C. The reaction products II can be thus isolated or the N,N-dimethylformamidine moiety can be cleaved during the acidic aqueous work up to produce the aminopyridines M which are isolated per crystallization or chromatography.

Besides deprotection under acidic conditions, the N,N-dimethylformamidine protecting group in compounds II can be removed using basic conditions which are even more compatible with the presence of an alkyne moiety, such as sodium hydroxide, ammonium hydroxide or ethylenediamine (J. Org. Chem., 2008, 73 (22), 8954-8959).

Alternatively, the imidazo[1,2-a]pyridines J can be cross coupled with III in the presence of a palladium source, a ligand, a base and optionally of other additives. As palladium source is used preferably a stable palladium salt or complex such as Pd(OAc)$_2$, Pd(OPiv)$_2$, PdCl$_2$[(t-Bu)$_2$PCl]$_2$, tetrakis(triphenylphosphine)palladium, bis(triphenylphosphinepalladium) dichloride. As a ligand a phosphine ligand is used such as triphenylphosphine, (4-CF$_3$—C$_6$H$_4$)$_3$P, (4-F—C$_6$H$_4$)$_3$P, (4-MeOC$_6$H$_4$)$_3$P, (2-MeC$_6$H$_4$)$_3$P, cHex$_3$P, tBuXPhos, BrettPhos, RuPhos, (PhO)$_3$P, di(1-adamantyl)-n-butylphosphine. Preferred ligand are triphenylphosphine or di(1-adamantyl)-n-butylphosphine. As base an appropriate base such as an inorganic base such as Cs$_2$CO$_3$, K$_2$CO$_3$ or (NH$_4$)$_2$CO$_3$, and preferably Cs$_2$CO$_3$. As an additive pivalic acid, isobutyric acid or mNO$_2$C$_6$H$_4$COOH may be used. The reaction is carried out in a polar solvent such as DMSO, DMF, NMP, nBuOH, dioxane, DMPU and preferably DMSO at a temperature of 50-130° C. and preferably at 90° C. to 120° C. The reaction products II are isolated per crystallization or chromatography.

Preparation of M3: 5-(2-Methyl-imidazo[1,2-a]pyridin-3-yl)-6-phenylethynyl-pyridin-2-ylamine

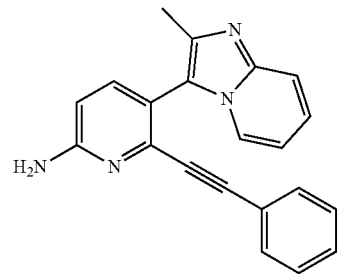 [SMILES: Cc1nc2ccccn2c1-c1ccc(N)nc1C#Cc1ccccc1]

Compound K1 (3.46 g, 13.41 mmol) is suspended in dry THF (8 mL). The mixture is cooled to 0° C. and treated with 1.3 M isopropylmagnesium chloride lithium chloride complex solution in THF (11.5 mL, 14.95 mol). After stirring for 1 h at this temperature 1.9 M zinc chloride solution in Me-THF (8.0 mL, 15.20 mmol) is added and the temperature is set to 20° C. The resulting solution of the zinc reagent is added over 30 min to a mixture of compound III-3 (2.0 g, 6.09 mmol), bis(dibenzylidene-acetone)palladium(0) (105 mg, 0.18 mmol) and RuPhos (170 mg, 0.36 mmol) in dry THF (8 mL) at 45-50° C., rinsing with dry THF (4 mL), and the reaction mixture is stirred overnight at this temperature. The reaction mixture is cooled to 20° C. and treated with 4 N of aqueous hydrochloric acid (10 mL) and water (14 mL). The organic phase is separated and the aqueous phase basified with aqueous ammonia and extracted with DCM. The combined extracts are evaporated and the residue dissolved in a mixture of ethanol (14 mL), 4 N aqueous hydrochloric acid (10 mL) and water (4 mL). The reaction mixture is stirred overnight at 45-50° C. and 4 N aqueous hydrochloric acid (5 mL) is again added. The reaction mixture is set to 75-80° C. and stirred at this temperature for 4 h. The title product M3 is isolated upon adjusting the pH to 5 and is isolated by filtration, contaminated with some 2-methylimidazo[1,2-a]pyridine. Yield: 80%. MS (ESI⁺) m/z=325 [M+H]⁺

Preparation of II-1: N'-{5-[2-(2-Methoxy-pyridin-3-yl)-7-methyl-imidazo[1,2-a]pyridin-3-yl]-6-quinolin-6-ylethynyl-pyridin-2-yl}-N,N-dimethyl-formamidine

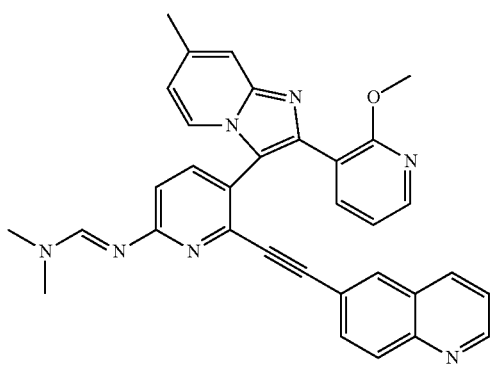 [SMILES: COc1ncccc1-c1nc2cc(C)ccn2c1-c1ccc(/N=C/N(C)C)nc1C#Cc1ccc2ncccc2c1]

Compound III-1 (360 mg, 0.95 mmol) is combined with 2-methoxy-3-{7-methylimidazo[1,2-a]pyridin-2-yl}pyridine J2 (295 mg, 1.23 mmol), pivalic acid (30 mg, 0.29 mmol), Pd(OAc)₂ (4.3 mg, 0.019 mmol), triphenylphosphine (20.0 mg, 0.076 mmol) and Cs₂CO₃ (325.0 mg, 1.00 mmol). DMSO (5 mL) is added and the mixture degassed with argon and stirred at 120° C. overnight. The reaction mixture is diluted with water (10 mL) and extracted with a mixture of ethyl acetate (5 mL) and 2-methyltetrahydrofurane (10 mL). The organic phase is washed with water (7 mL) and concentrated. The residue is purified on silica gel to yield the title compound. Yield: 29%. MS (ESI⁺) m/z=538 [M+H]⁺.

Preparation of 2-methoxy-3-{7-methylimidazo[1,2-a]pyridin-2-yl}pyridine J2 is reported in US 2013/0225567.

The following compounds II-2 to II-5 can be prepared under analogous conditions starting from the corresponding building blocks III and J (analogous conditions include potential deviations from the disclosed conditions in terms of, e.g., solvent, reaction conditions or purification which the skilled artisan is familiar with and takes into account).

II-2

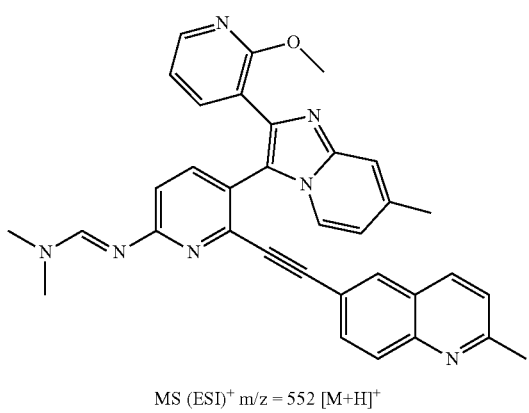

MS (ESI)⁺ m/z = 552 [M+H]⁺

II-3

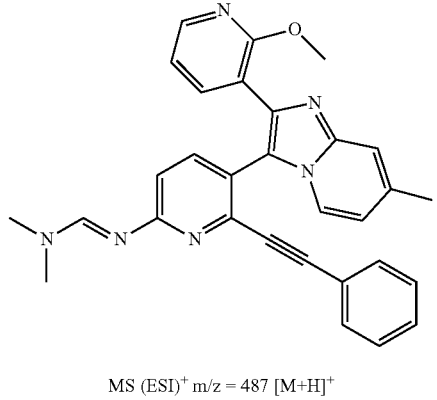

MS (ESI)⁺ m/z = 487 [M+H]⁺

II-4

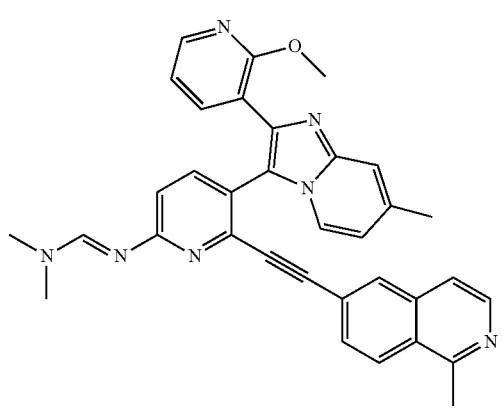

MS (ESI)⁺ m/z = 552 [M+H]⁺

II-5

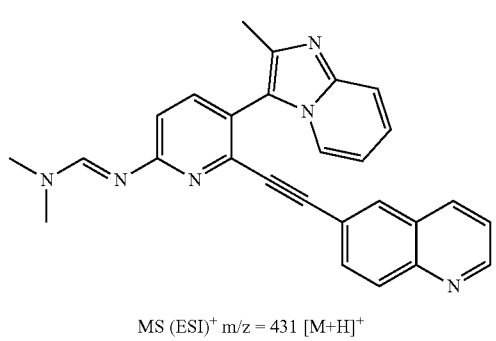

MS (ESI)⁺ m/z = 431 [M+H]⁺

Preparation of Intermediates M: Formamidine Cleavage

The formamidine protecting group present in compounds II can be removed under aqueous acidic or basic conditions.

The following compounds M1, M2 and M4 to M6 can be obtained by deprotection of precursors II.

M1

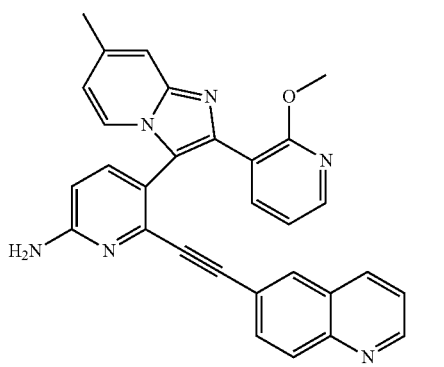

MS (ESI⁺) m/z = 483 [M+H]⁺

M2

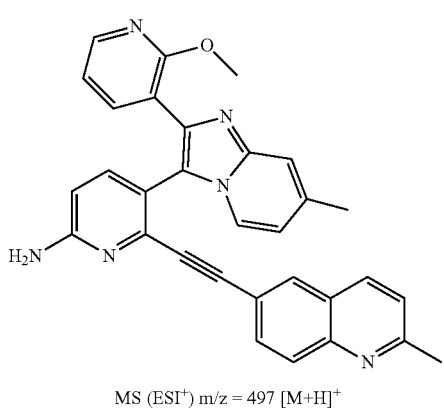

MS (ESI⁺) m/z = 497 [M+H]⁺

M4

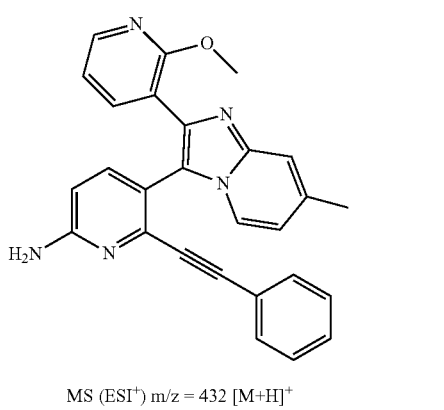

MS (ESI⁺) m/z = 432 [M+H]⁺

M5

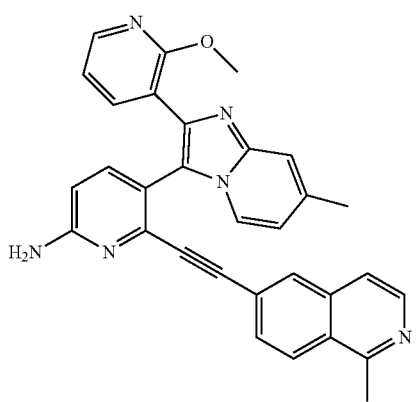

MS (ESI⁺) m/z = 497 [M+H]⁺

-continued

M6

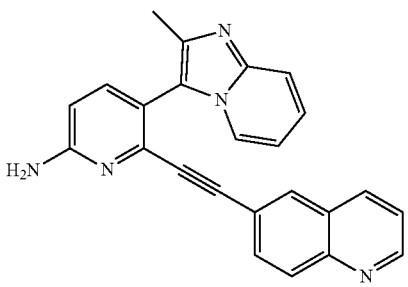

MS (ESI⁺) m/z = 376 [M+H]⁺

Compounds M can be further functionalized at the 2-amino moiety, e.g. by acylation with an appropriate protected aminoacid, to produce SMAC mimetics compounds as those reported in the patent US 2013/0225567 using the general method reported on page 23.

Alternative methods for amide formation starting from the appropriate protected amino acid can also be used. Preferably a combination of T3P (Propylphosphonic Anhydride) in an organic solvent such as dichloromethane, pyridine, tetrahydrofurane, acetonitrile, ethyl acetate or mixture thereof at a temperature of −30-+30° C., preferably at −20/−15° C.

Preparation of N3: Methyl-{1-[5-(2-methyl-imidazo[1,2-a]pyridin-3-yl)-6-phenylethynyl-pyridin-2-yl-carbamoyl]-ethyl}-carbamic acid tert-butyl ester

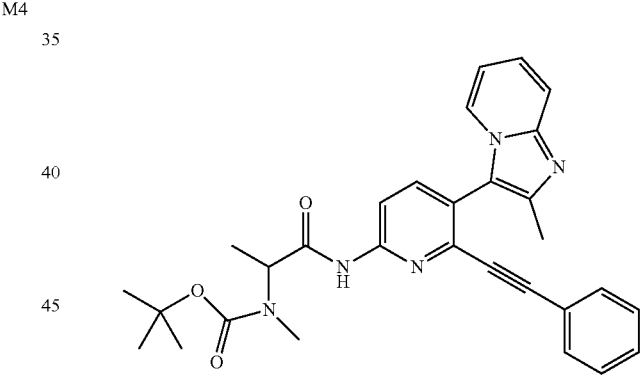

A mixture of 2-[methyl-[(2-methylpropan-2-yl)oxycarbonyl]amino]propanoic acid (15 mg, 0.074 mmol), N,N'-dicyclohexylcarbodiimide (7.6 mg, 0.074 mmol) and DIPEA (6.3 µL, 0.037 mmol) in DCM (0.5 mL) is stirred at room temperature for 30 minutes. Compound M3 (6 mg, 0.018 mmol) is added and the mixture stirred at 60° C. overnight. After this time according to HPLC-MS analysis 60% of the title product N3 (MS (ESI⁺) m/z=510 [M+H]⁺) is formed.

Deprotection of the Boc-protective groups can be performed as described in WO 2013/127729 and WO 2016/023858.

The following compounds N1, N2 and N4 to N6 can be prepared under analogous conditions by amide coupling of precursors M (analogous conditions include potential deviations from the disclosed conditions in terms of, e.g., solvent, reaction conditions or purification which the skilled artisan is familiar with and takes into account).

N1
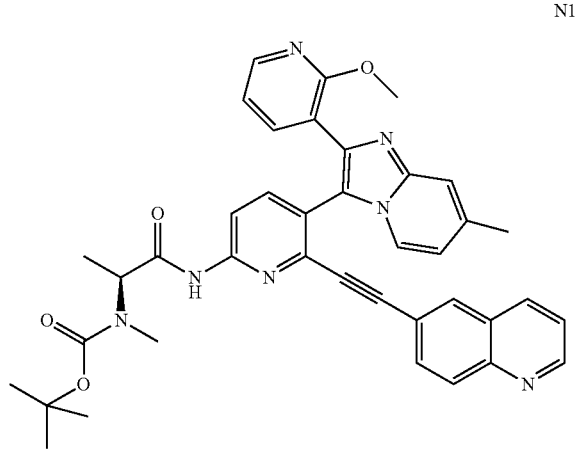
MS (ESI⁺) m/z = 668 [M+H]⁺
N2
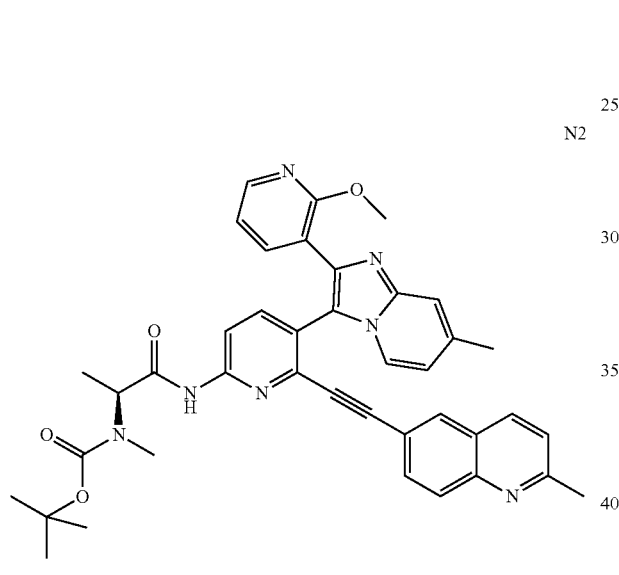
MS (ESI⁺) m/z = 682 [M+H]⁺
N4
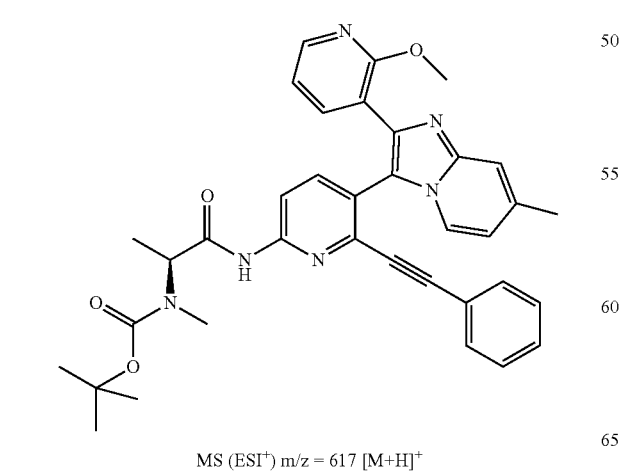
MS (ESI⁺) m/z = 617 [M+H]⁺
N5
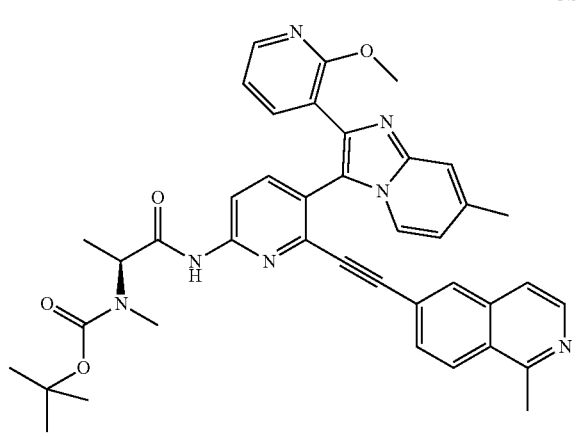
MS (ESI⁺) m/z = 682 [M+H]⁺
N6
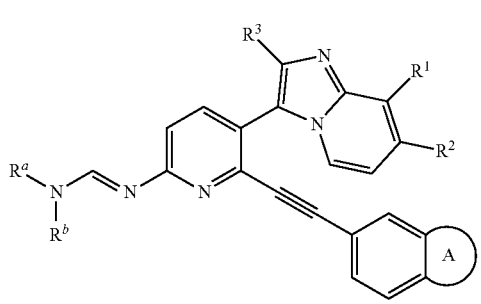
MS (ESI⁺) m/z = 561 [M+H]⁺
The invention claimed is:
1. A process for the synthesis of a compound of formula
(II)
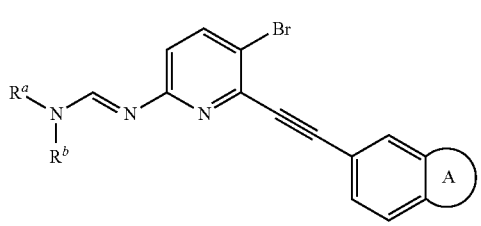
comprising the step of
preparing the compound of formula
(III)

according to a process comprising the steps of:
obtaining the compound of formula

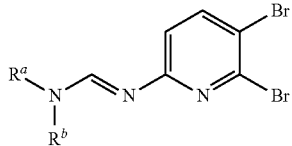
(B)

by reacting 5,6-dibromo-pyridin-2-yl-amine with a 1,1-dialkoxy-N,N-dialkylmethyl-amine of the formula $(R^zO)_2$—CHN($R^a$,$R^b$), wherein $R^z$ is a —$C_{1-3}$alkyl group;
and reacting the compound of formula

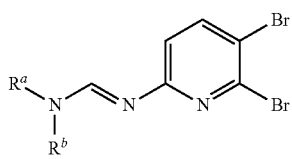
(B)

with a compound of formula

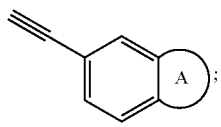
(E)

reacting the resulting compound of formula (III)

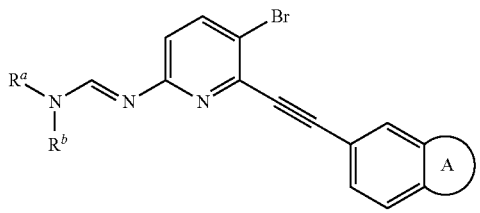
(III)

with a compound of formula

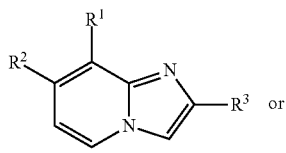
(J)

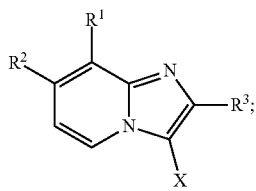
(K)

wherein
A is one of the following two fused rings:

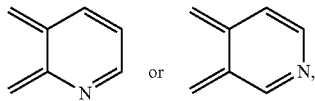

each optionally substituted with a —$C_{1-3}$alkyl group;
$R^1$ is selected from hydrogen, —$C_{1-3}$alkyl and halogen;
$R^2$ is selected from hydrogen, —$C_{1-3}$alkyl and halogen;
$R^3$ is selected from —$C_{1-3}$alkyl and pyridyl optionally substituted with —$C_{1-3}$alkyl or —O—$C_{1-3}$alkyl;
X is halogen;
$R^a$ and $R^b$ are the same or different selected from —$C_{1-4}$alkyl and —$CH_2$-phenyl.

2. A process for the synthesis of a compound of formula

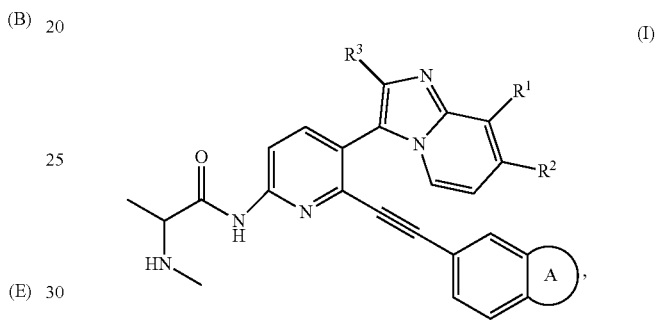
(I)

wherein
A is one of the following two fused rings:

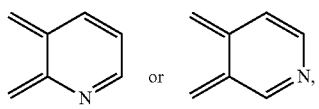

each optionally substituted with a —$C_{1-3}$alkyl group;
$R^1$ is selected from hydrogen, —$C_{1-3}$alkyl and halogen;
$R^2$ is selected from hydrogen, —$C_{1-3}$alkyl and halogen;
$R^3$ is selected from —$C_{1-3}$alkyl and pyridyl optionally substituted with —$C_{1-3}$alkyl or —O—$C_{1-3}$alkyl;
comprising the steps of
preparing the compound of formula

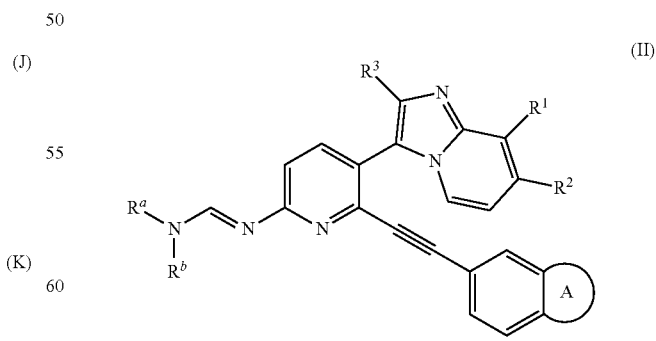
(II)

according to the process of claim 1;
wherein
$R^a$ and $R^b$ are the same or different selected from —$C_{1-4}$alkyl and —$CH_2$-phenyl;

deprotecting the compound of formula II to form a compound of formula (M)

forming a compound of formula (N)

by coupling a compound of formula M with 2-[methyl-[(2-methylpropan-2-yl)oxycarbonyl]amino]propanoic acid, wherein the 2-[methyl-[(2-methylpropan-2-yl)oxycarbonyl]amino]propanoic acid is racemic, (S)-2-[methyl-[(2-methylpropan-2-yl)oxycarbonyl]amino]propanoic acid or (R)-2-[methyl-[(2-methylpropan-2-yl)oxycarbonyl]amino]propanoic acid;

deprotecting the compound of formula (N)

to obtain the compound of formula (I)

3. The process according to claim 1, further comprising the steps of cyclizing a compound of formula (C)

to obtain a compound of formula (J)

and, optionally, further reacting compound of formula (J) to obtain a compound of formula (K)

wherein $Y^-$ is $Br^-$ or $Cl^-$;

$R^1$ is selected from hydrogen, —$C_{1-3}$alkyl and halogen;

$R^2$ is selected from hydrogen, —$C_{1-3}$alkyl and halogen;

$R^3$ is —$CH_2$—$C_{1-2}$alkyl;

$R^4$ is selected from hydrogen and $C_{1-2}$alkyl;

X is halogen.

4. The process of claim 1, wherein $R^1$ is selected from hydrogen, —$C_{1-3}$alkyl and $R^2$ is selected from hydrogen, —$C_{1-3}$alkyl and $R^3$ is selected from —$C_{1-3}$alkyl and pyridyl optionally substituted with —$C_{1-3}$alkyl or —O—$C_{1-3}$alkyl.

5. A compound of formula (II)

(II)

wherein
A is one of the following two fused rings:

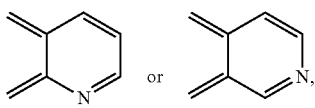

each optionally substituted with a —$C_{1-3}$alkyl group;
R$^1$ is selected from hydrogen, —$C_{1-3}$alkyl and halogen;
R$^2$ is selected from hydrogen, —$C_{1-3}$alkyl and halogen;
R$^3$ is selected from —$C_{1-3}$alkyl and pyridyl optionally substituted with —$C_{1-3}$alkyl or —O—$C_{1-3}$alkyl;
R$^a$ and R$^b$ are the same or different selected from —$C_{1-4}$ alkyl and —CH$_2$-phenyl;
or a salt thereof.

6. A compound or a salt thereof according to claim 5 selected from among

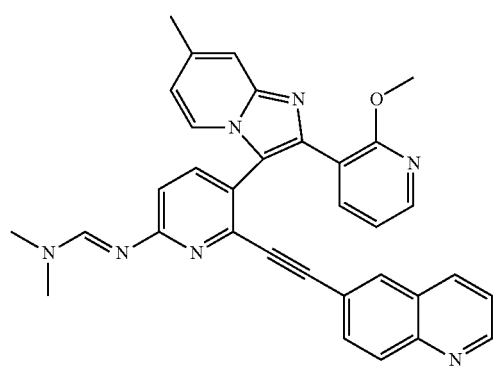

II-1

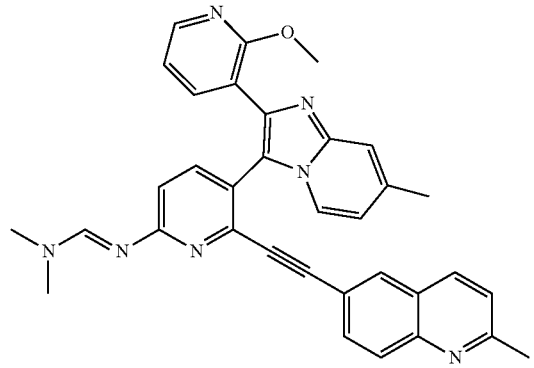

II-2

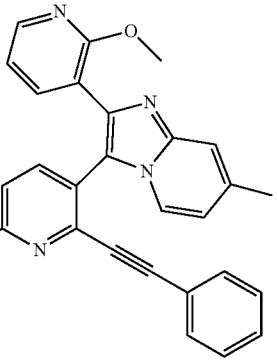

II-3

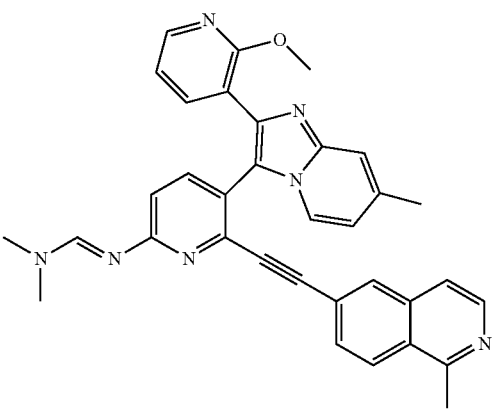

II-4

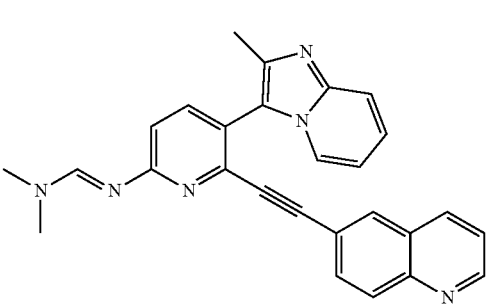

II-5

* * * * *